United States Patent
Dam et al.

(10) Patent No.: US 8,280,126 B2
(45) Date of Patent: Oct. 2, 2012

(54) CARTILAGE CURVATURE

(75) Inventors: Erik B. Dam, Copenhagen (DK); Jenny Folkesson, San Francisco, CA (US); Paola Pettersen, Koege (DK); Ole F. Olsen, Vaerloese (DK); Mads Nielsen, Dragoer (DK); Claus Christiansen, Morcote (CH)

(73) Assignee: Synarc Inc., Newark, CA (US)

( * ) Notice: Subject to any disclaimer, the term of this patent is extended or adjusted under 35 U.S.C. 154(b) by 815 days.

(21) Appl. No.: 12/083,800

(22) PCT Filed: Sep. 4, 2006

(86) PCT No.: PCT/EP2006/008606
§ 371 (c)(1),
(2), (4) Date: Mar. 12, 2009

(87) PCT Pub. No.: WO2007/048463
PCT Pub. Date: May 3, 2007

(65) Prior Publication Data
US 2009/0190815 A1 Jul. 30, 2009

(30) Foreign Application Priority Data
Oct. 24, 2005 (GB) .................................. 0521640.3

(51) Int. Cl.
*G06K 9/00* (2006.01)
(52) U.S. Cl. ....................................... 382/128; 382/132
(58) Field of Classification Search .................. 382/128, 382/132; 600/407
See application file for complete search history.

(56) References Cited

U.S. PATENT DOCUMENTS

| | | | |
|---|---|---|---|
| 6,799,066 B2 * | 9/2004 | Steines et al. | 600/407 |
| 6,836,557 B2 * | 12/2004 | Tamez-Pena et al. | 382/128 |
| 2004/0075655 A1 | 4/2004 | Dunnett | |
| 2004/0167390 A1 | 8/2004 | Alexander | |
| 2005/0113663 A1 | 5/2005 | Tamez-Pena | |

OTHER PUBLICATIONS

T.C. Dunn et al., "T2 Relexation Time of Cartilage at MR Imaging: Comparison with Severity of Knee Osteoarthritis", *Radiology*, 232:2, pp. 592-598 (2004).
S. Amin et al., "The relationship between cartilage loss on magnetic resonance imaging and radiographic progression in men and women with knee osteoarthritis", *Arthritis and Rhematism*, 52:10, pp. 3152-3159 (Oct. 2005).
H. Graichen et al., "Quantitative Assessment of Cartilage Status in Osteoarthritis by Quantitative Magnetic Resonance Imaging", *Arthritis & Rheumatism*, 50:3, pp. 811-816 (Mar. 2004).
D. Loeuille et al., "Magnetic Resonance Imaging of Normal and Osteoarthritic Cartilage", *Arthritis & Rheumatism*, 41:6, pp. 963-975 (Jun. 1998).
D.T. Felson et al., "The effect of body weight on progression of knee osteoarthritis is dependent on alignment", *Arthritis & Rheumatism*, 50:12, pp. 3904-3909 (Dec. 2004).

(Continued)

*Primary Examiner* — Louis Arana
(74) *Attorney, Agent, or Firm* — Edwards Wildman Palmer LLP; Peter C. Lauro, Esq.

(57) ABSTRACT

A method for the analysis of three dimensional scan data representing an articular cartilage is provided to extract a quantitative parameter indicative of joint pathology. A measure of local curvature of the cartilage is determined within a region of interest. The value of the quantitative parameter of this joint derived from this measure is compared with the value of a similar quantitative parameter previously established in respect of healthy joints and/or joints characterized by a pathology.

24 Claims, 11 Drawing Sheets

OTHER PUBLICATIONS

S. Hinterwimmer et al., "Cartilage atrophy in the knees of patients after seven weeks of partial load bearing", *Arthritis & Rheumatism*, 50:8, pp. 2516-2520 (Aug. 2004).

J. Hohe et al., "Surface size, curvature analysis, and assessment of knee joint incongruity with MRI in vivo", *Magnetic Resonance in Medicine*, vol. 47, pp. 554-561 (2002).

S. Koo M.S. et al., "Considerations in measuring cartilage thickness using MRI: factors influencing reproducibility and accuracy", *Osteoarthritis and Cartilage*, vol. 12, pp. 782-789 (2005).

E.A. Messent, Ph.D. et al., "Tibial cancellous bone changes in patients with knee osteoarthritis. A short-term longitudinal study using Fractal Signature Analysis", *Osteoarthritis and Cartilage*, vol. 13, pp. 463-470 (2005).

C. Ding, M.D. et al., "Knee cartilage defects: association with early radiographic osteoarthritis, decreased cartilage volume, increased joint surface area and type II collagen breakdown", *Osteoarthritis and Cartilage*, vol. 13, pp. 198-205 (2005).

E.J. McWalter D.Sc. et al., "Use of novel interactive input devices for segmentation of articular cartilage from magnetic resonance images", *Osteoarthritis and Cartilage*, vol. 13, pp. 48-53 (2005).

E. Abadie et al., "Recommendations for the use of new methods to assess the efficacy of disease-modifying drugs in the treatment of osteoarthritis", *Osteoarthritis and Cartilage*, vol. 12, pp. 263-268 (2004).

G. Jones, M.D. et al., "Early radiographic osteoarthritis is associated with substantial changes in cartilage volume and tibial bone surface area in both males and females", *Osteoarthritis and Cartilage*, vol. 12, pp. 169-174 (2004).

G. Tracton et al., "MASK: combining 2D and 3D segmentation methods to enhance functionality", *SPIE*, vol. 2299, pp. 98-109 (1994).

S. Arya et al., "An optimal algorithm for approximate nearest neighbor searching in fixed dimensions", *Journal of the ACM*, 45:6, pp. 891-923 (Nov. 1998).

H. Blum et al., "Shape description using weighted symmetric axis features", *Pattern Recognition*, vol. 10, pp. 167-180 (1978).

T.F. Cootes et al., "Active Shape Models—Their Training and Application", *Computer Vision and Image Understanding*, 61:1, pp. 38-59 (1995).

R.H. Davies et al., "A Minimum Descdription Length Approach to Statistical Shape Modeling", *IEEE Transactions on Medical Imaging*, 21:5, pp. 525-537 (May 2002).

P.T. Fletcher et al., "Caussian Distributions on Lie Groups and Their Application to Statistical Shape Analysis", *Information Processing in Medical Imaging,*, pp. 450-462 (2003).

S. Joshi et al., "Multiscale deformable model segmentation and statistical shape analysis using medial descriptions", *IEEE Transactions on Medical Imaging*, 21:5, pp. 538-550 (May 2002).

M. Kass et al., "Snakes: Active Contour Models", *International Journal of Computer Vision*, pp. 321-331 (1988).

J.A. Lynch et al., "Automating measurement of subtle changes in articular cartilage from MRI of the knee by combining 3D image registration and segmentation", *SPIE Medical Imaging*, vol. 4322, pp. 431-439 (2001).

S.M. Pizer et al., "Segmentation, Registration, and Measurement of Shape Variation via Image Object Shape", *IEEE Transactions on Medical Imaging*, 18:10, pp. 851-865 (Oct. 1999).

J.H. Kellgren et al., "Radiological Assessment of Osteo-Arthrosis", *Ann Rheum Dis.*, vol. 16, pp. 494-502 (1957).

Andrew Thall, "Fast $C^2$ Interpolating Subdivision Surfaces using Iterative Inversion of Stationary Subdivision Rules", *Technical Report—University of North Caroline*, pp. 1-30 (Jan. 2003).

V. Grau et al., "Improved watershed transform for medical image segmentation using prior information", *IEEE Transactions on Medical Imaging*, 23:4, pp. 447-458 (Apr. 2004).

P.T. Fletcher et al., "Statistic of Shape via Principal Geodesic Analysis on Lie Groups", Proceedings of the 2003 IEEE Computer Society Conference on Computer Vision and Pattern Recognition (CVPR'03), (2003).

D. Cremers et al., "Nonlinear Shape Statistics in Mumford-Shah Based Segmentation", *7th European Conference on Computer Vision*, vol. 2351, pp. 93-108 (2002).

T. Stammberger et al., "Interobserver Reproducibility of Quantitative Cartilage Measurements: Comparison of B-Spline Snales and Manual Segmentation", *Magnetic Resonance Imaging*, 17:7, pp. 1033-1042 (1999).

M. Terukina, M.D. et al., "Analysis of th ethickness and Curvature of Articular Cartilage of the Femoral Condyle", *Athroscopy: The Journal of Arthroscopic and Related Surgery*, 19:9, pp. 969-973 (Nov. 2003).

S.K. Pakin et al., "Segmentation, surface extraction and thickness computation of articular cartilage", *SPIE Medical Imaging*, vol. 4684, pp. 155-166 (2002).

J.G. Tamex-Pena et al., "Knee Cartilage Extraction and Bone-Cartilage Interface Analysis from 3D MRI Data Sets", *SPEI Medical Imaging*, vol. 5370, pp. 1774-1784 (2004).

S.M. Pizer et al., "Deformable *M-Reps* for 3D Medical Image Segmentation", *International Journal of Computer Vision*, 55(2/3), pp. 85-106 (2003).

H.H. Thodberg et al., "Minimum Description Length Shape and Appearance Models", *LNCS*, pp. 51-62 (2003).

C. Buckland-Wright D.Sc et al., "Subchondral bone changes in hand and knee osteoarthritis detected by radiography", *Osteoarthritis and Cartilage*, vol. 12, pp. S10-S19 (2004).

J. Folkesson et al., "Automatic Segmentation of the Articular Cartilage in Knee MRI Using a Hierarchical Multi-class Classification Scheme", *LNCS 3749,*, pp. 327-334 (2005).

E. Dam et al., "Prostate Shape Modeling Based on Principal Geodesic Analysis Bootstrapping", *LNCS 3217*, pp. 1008-1016 (2004).

H.H. Thodberg et al., "Adding Curvature to Minimum Description Length Shape Models", *Proc of British Machine Vision Conference* (2003).

Lee R. Dice, "Measures of the Amount of Ecologic Association Between Species", *Ecology*, vol. 26, pp. 297-302 (1945).

J. Folkesson et al., "Automatic Segmentation of the Articular Cartilage in Knee MRI Using a Hierarchial Multi-class Classificiation Scheme", *LNCS 3749*, pp. 327-334 (2005).

L. Kamibayashi et al., "Changes in Mean Trabecular Orientation in the Medial Condyle of the Proximal Tibia in Osteoarthritis", *Calcif Tissue Int.*, vol. 57, pp. 69-73 (1995).

J. Folkesson et al., "Locating Articular Cartilage in MRI Images", *Medical Imaging 2005: Proceedings of the SPIE*, vol. 5747, pp. 14841490 (2005).

O.J. Muensterer et al., "Computer-aided three dimensional assessment of knee-joint cartilage with magnetic resonance imaging", *Clinical Biomechanics*, 11:5, pp. 260-266 (1996).

J. Folkesson et al., "Automatic Quantification of Articular Cartilage from Knee MR Scans Using Surface Smoothness as Osteoarthritis Indicator", *ICCV, Computer Vision for Biomedical Image Applications: Current Techniques and Future Trends*, 13:1, p. S125 (2005).

Eckstein, F., et al. "In Vivo Morphometry and Functional Analysis of Human Articular Cartilage with Quantitative Magnetic Resonance Imaging—From Image to Data, From Data to Theory" Anatomy and Embryology 203(3) 147-143 (2001).

Hohe, J., et al. "Surface Size, Curvature Analysis, and Assessment of Knee Join Incongruity with MRI in Vivo" *Magnetic Resonance in Medicine* 47(3): 554-561 (2002).

Form PTO/ISA/210 issued in PCT/EP2006/008606, May 12, 2006, Nordic Bioscience A/S.

Form PTO/ISA/237 issued in PCT/EP2006/008606, May 12, 2006, Nordic Bioscience A/S.

* cited by examiner a    b a  b a b a b a b

CARTILAGE CURVATURE

This application is the U.S. national phase, pursuant to 35 U.S.C. §371, of PCT International application Ser. No. PCT/EP2006/008606, field Sep. 4, 2006, designating the United States and published in English on May 3, 2007 as publication WO 2007/048463 A1, which claims priority to United Kingdom application Ser. No. GB 0521640.3, filed Oct. 24, 2005.

The present invention relates to a method for deriving a useful quantitative measure indicative of joint pathology from three dimensional scan data of a joint cartilage, e.g. of a knee joint, which may be useful in the diagnosis and prognosis of said pathology, especially of osteoarthritis.

Osteoarthritis (OA) affects the daily lives of the majority of the older part of the world population—for some by minor morning stiffness and for others to the degree of causing severe pain and reduced range of motion. Furthermore, even though promising new treatment possibilities are arising, a major, thoroughly documented breakthrough in effective treatment of OA beyond symptom control is still awaited. One limiting factor in the development and evaluation of new treatments is the effectiveness of the methods for quantification of disease progression in clinical studies.

Accuracy and precision of quantification methods are essential, together with the ability to monitor the actual progression of the disease. These factors, accuracy and precision (accuracy is used to mean correctness whereas precision is used for reproducibility), affect both the number of test subjects needed in a clinical study and the required duration of the study. In addition to accuracy and precision, there is very substantial value in automating quantification methods. Fully automatic (typically computer based) quantification methods by definition eliminate intra-observer variation and thereby potentially allow better precision. Furthermore, for studies based on medical imaging data (X-ray, MRI, CT, etc.), the load on the radiologists is potentially overwhelming—and increasingly so when morphometric measures in 3D are desired. Morphometric measures require fully segmented structures with anatomical correspondence defined. Thereby, computer-based methods can not only relieve the radiologists but also allow quantification measures that would otherwise be unfeasible in large-scale studies or simply even impossible.

In the detailed illustrative description of the present invention, we shall focus on quantification of articular knee cartilage from Magnetic Resonance Imaging (MRI) by way of example with particular reference to OA. This is without limitation of the general scope of the invention either as regards imaging technology, joint of interest, or relevant pathology but will aid ready understanding. MRI offers some obvious advantages compared to traditional X-ray based OA monitoring. First, the cartilage is visible. Secondly, the 3D scans allow morphometric analysis.

We introduce morphometric measures extracted using a novel, fully-automatic computer-based method. The measures quantify the shape of the cartilage sheet in terms of thickness and curvature or 'tension'. Thickness is a natural measure for quantifying focal cartilage breakdown. 'Tension' (or curvature as this feature will herein after be referred to) is a quantification of the bending of the cartilage sheet over a region of interest. The bending is quantified as a summation of the shape rather than of the local cartilage sheet or cartilage surface. It therefore provides a quantification of the shape rather than of the cartilage breakdown. It may derive as much or more from changes in the underlying bone as to changes in the structure or amount of the cartilage itself.

Other methods exist for segmentation and quantification of articular cartilage from MRI data. However, to our knowledge, no other fully automatic method has been evaluated and published. In general, the MR based methods are more often evaluated for segmentation accuracy and precision rather than for morphometric quantification and ability to monitor OA progression.

A semi-automatic method based on watershed transformation and requiring 5-10 minutes of human interaction per knee is presented in (Grau, Mewes, Alcaniz, Kikinis & Warfield 2004) showing good segmentation performance on four knees.

Another method performs region growing based on voxel intensities from fused scans followed by classification and editing of the resulting regions requiring 10-40 minutes of human interaction per knee (Pakin, Tamez-Pena, Totterman & J. Parker 2002, Tamez-Pena, Barbu-McInnis & Totterman 2004). The method is sparsely evaluated but thickness measures repeated on the same scan results in a CV of 3.2% for the tibial medial compartment.

Also, some methods perform cartilage segmentation by slice-wise 2D segmentation (Stammberger, Eckstein, Michaelis, Englmeier & Reiser 1999, Lynch, Zaim, Zhao, Stork, Peterfy & Genant 2001). They rely on experts marking the cartilage sheet in most slices and thereby become quite time-consuming (about 2.5 hours per knee (Stammberger et al. 1999)). Furthermore, the resulting segmentations are less suitable for morphometric analysis.

The method from (Stammberger et al. 1999) is evaluated in (Koo, Gold & Andriacchi 2005) on four test subjects giving a coefficient of variation (CV) for cartilage thickness measurement of 6.6% for inter-observer variability and about 4% relative difference between measurements from repeated scans of a single test subject.

In McWalter, Wirthz, Siebert, von Eisenhart-Rothe, Hudelmaier, Wilson & Eckstein 2005, they report a reproducibility of tibial cartilage thickness measurements as a CV of around 5%. This is from a fully manual segmentation using approximately 1 hour per knee of 6 test subjects.

Another semi-automatic method based on region growing is used in (Ding, Garnero, Cicuttini, Scott, Cooley & Jones 2005) where they show that cartilage volume is significantly related to presence of cartilage defects in a study including 372 test subjects. No morphometric analysis is performed.

Methods focusing on measurement of the joint space width from radiographs have been extensively evaluated in clinical studies.

U.S. Pat. No. 6,560,476 discusses a method and system for assessing a joint of a patient by taking a three-dimensional magnetic resonance image of the joint, identifying a biomarker in the image using statistical segmentation and motion tracking and deriving a quantitative measurement of the biomarker and storing an identification of the biomarker, the quantitative measurement and the image in a storage medium. The biomarker is a bone or joint characteristic, a surface topology of cartilage shape, cartilage surface or surface characteristics, or cartilage volume.

WO03/012724 discusses automatic processing of scan images to extract measurements of biomarkers. Semi-automatic segmentation of images is described and an attempt is made to track biomarkers through time on subsequent scans. A large number of biomarkers are mentioned, including the mean and standard deviation of the local curvature of the cartilage surface, given as an example of a cartilage surface topology biomarker. However, whilst it is indicated that it may be of interest to track changes in such topological measures through time, there is no suggestion that the value for a given patient at any one time could be compared in a diagnostically meaningful way with values from other individuals. There is moreover no clinical data provided to show that this parameter does actually change with disease progression. Accordingly, it cannot be deduced from this teaching that it would be diagnostic to compare a value of local curvature of a cartilage obtained from a patient to equivalent values established in respect of a population of pathology free individuals or a population of patients suffering from a cartilage pathology. Indeed, it is not even deducible from this teaching whether a higher or a lower value for such curvature should be regarded as more pathological.

(Hohe, J., Ateshian, G., Reiser, M., Englmeier, K. K., Eckstein, F.) have in a study analysed the curvature of knee cartilage surfaces from magnetic resonance images as an incongruity measure, by first segmenting the cartilage slice-by-slice using b-splines then estimating the principal curvatures locally by interpolating a b-spline on a 5×5 neighbourhood of surface points 6 mm apart and use b-spline derivatives to form the Weingarten matrix. They scanned 14 healthy volunteers 4 times and found an average mean curvature of 29.6 m$^{-1}$ (±9.9 m$^{-1}$ s.d) for the total tibial medial cartilage surface and 0.9 m$^-$(±3.8 m$^{-1}$ s.d) for the central part of the same cartilage surface, with inter-scan reproducibility values up to 4.7 m$^-$root mean squared s.d. The precision of this method is found to provide reliable discrimination between different knee joint surface, but not between person to person.

(Terukina, M., Fujioka, H., Yoshiya, S., Kurosaka, M., Makino, T., Matsui, N., Tanaka, J.) performed an in-vitro study of the curvature in 2D by slicing the knee joint through the sagittal plane and fitting a circle to three equidistant points within 1 cm on the cartilage surface then taking the inverse of the radius for the curvature. They found an average curvature of 4.4 m$^{-1}$ for the femoral condyle in their study intended for cartilage replacement. Terukina et al. keep a constant distance between points (d=0.5 cm) for their circle estimates. By not shrinking the distance at high curvature, two points can be placed at the same approximate location giving an upper bound for the curvature value of $(d/2)^{-1}$=400 m$^-$for d=0.5 cm, giving only a crude estimate at low scales (high resolution). Furthermore, as only 2D curvature is used, curvature can only be estimated in the selected plane of view.

The present invention now provides, in a first aspect, a method for the analysis of three dimensional scan data representing an articular cartilage to extract a quantitative parameter indicative of joint pathology, which method comprises determining a measure of the local curvature of the cartilage within a region of interest, and further comprising comparing the measured value of said quantitative parameter for the joint with values of the quantitative parameter previously established in respect of healthy joints and/or in respect of joints characterised by a pathology.

Preferably, the method comprises determining a measure of the 3D local curvature at a scale arranged to result in a measure of curvature above 40 m$^{-1}$ and in some embodiments, with an upper limit of 200 m$^{-1}$.

The region of interest is preferably selected such that it lies in a load bearing area of said cartilage. Suitably, it is selected to lie in an interior region of a cartilage sheet separated from the edges of said sheet.

Whilst the invention is applicable to any joint cartilage, for instance cartilage of the hip joint, finger joints, vertebra cartilage, shoulder joints or elbow joints, the cartilage is preferably a knee cartilage, especially a tibial cartilage and more especially a medial tibial cartilage.

Preferably, a comparison of said quantitative parameter is made both with values of the quantitative parameter previously established in respect of healthy joints and with values of said quantitative parameter previously established in respect of joints characterised by a pathology.

Said pathology is preferably osteoarthritis or rheumatoid arthritis, but may be pigmented villonodular synovitis, Lipoid dematoarthritis (Multicentric reticulohistiocytosis), Enteropathic arthritis, hemophilia (intraarticular bleeding), Gout, Familial Mediterranean fever, Pseudogout, Ochronotic arthropathy, Secondary OA, Syphilis (tabes dorsalis), Pyrogenic arthritis, Tuberculous arthritis or Fungal arthritis.

Whilst the invention is applicable to any 3-dimensional image data, however acquired, for instance from an NMR scan, or by X-ray tomography, it is preferred that said three dimensional scan data is produced by magnetic resonance imaging (MRI).

Said quantitative parameter is preferably derived from changes between adjacent locations within the region of interest in directions defined with respect to normals to a selected cartilage surface or interior contour. Thus, preferably it is changes between the directions of said normals as one moves from location to location within the region of interest that are quantified to produce said quantitative parameter.

Preferably, said quantitative parameter represents an average of said changes in direction over said region of interest. Suitably therefore, said quantitative parameter is quantitatively related to the average value over the region of interest of 'curvature(p)' given for each point p in the region of interest by the expression:

$$\text{curvature}(p) = \frac{1}{|N|} \sum_{n \in N} \arccos(\text{normal}(p) \cdot \text{normal}(n))$$

reflecting the mean angle between the surface normal at surface point p with a neighbourhood set N and the normals at the neighbouring surface points n. Said parameter may be given directly by said formula or may of course for instance be proportional to the direct value of said equation or may be the inverse of said direct value. Any other arithmetical manipulation of the direct value of the equation may be used.

For example, in one embodiment, we define the load bearing (central) part of the articular surface as a region of interest and estimate the curvature locally in a 5×5 neighbourhood by taking the angle between the normals and dividing it by the distance between them:

$$\text{curvature}(p) = \frac{1}{|N|} \sum_{n \in N} \frac{1}{\text{dist}(p, n)} \arccos(\text{normal}(p) \cdot \text{normal}(n))$$

Assuming short distances and small angles due to the regularisation, this is an approximation to the curvature, $$\kappa = \frac{d\theta}{ds},$$

where θ is the angle between two normals and s is the arc length. The average of the absolute values of local estimations κ of the boundary points in the region of interest is chosen as the quantitative curvature estimate.

Suitably points p are sampled at a spacing of from 0.2 to 2 mm, more preferably 0.25 to 1.25 mm, more preferably 0.5 to 1.0 mm, e.g. about 0.75 mm in evaluating said average value of curvature (p). The spacing between sampled points governs the extent to which very small surface texture features are allowed to contribute to the measured parameter.

Preferably therefore, said neighbourhood set N of neighbouring points for any point P occupies and area of from 1 mm$^2$ to 4 mm$^2$.

Preferably, the said region of interest is from 1 cm$^2$ to 8 cm$^2$ in area.

A method according to the invention may further comprise combining said measure of local curvature with one or more of (a) a measure of cartilage volume, (b) a measure of cartilage thickness, (c) a measure of cartilage smoothness and (d) a measure of narrowest joint gap, to provide an improved discrimination between said combined measure when representing joint pathology and equivalent measures derived from healthy joints.

A method according to the invention may further comprise analysing said scan data to perform an automatic segmentation of image data representing cartilage from bone and other background prior to extracting said quantitative parameter. Preferably, this is a fully automatic segmentation that involves no manual marking of features in the scan prior to the segmentation process being carried out by data processing apparatus.

Where the quantitative parameter is calculated as described herein or in an equivalent manner, a value for said quantitative parameter which is higher than that established for healthy joints is taken as indicative of probable joint pathology.

A measurement of local curvature may alternatively, at least in some part be regarded as a measurement of the variation in the thickness of the cartilage sheet, as it will not necessarily be the case that an outward bulge in one surface will be compensated in thickness terms by an inward, convex curving of the opposite surface. Rather, such an outward, convex bulge in one surface may represent a bending of the sheet or else a thickening of the sheet at that point. Accordingly, in an alternative aspect, the invention includes determining a quantitative measure of the variation of thickness of a cartilage within a region of interest.

In a further alternative aspect, the invention includes a method for the analysis of three dimensional scan data representing an articular cartilage to extract a quantitative parameter indicative of joint pathology, which method comprises determining a measure of the local curvature of the cartilage within a region of interest, wherein said quantitative parameter is derived from changes between adjacent locations within the region of interest in directions defined with respect to normals to a selected cartilage surface or interior contour, preferably, such that said quantitative parameter represents an average of said changes in direction over said region of interest. As in accordance with the first aspect of the invention, the quantitative parameter is suitably quantitatively related to the average value over the region of interest of 'curvature(p)' given for each point p in the region of interest by the expression:

$$\text{curvature}(p) = \frac{1}{|N|} \sum_{n \in N} \arccos(\text{normal}(p) \cdot \text{normal}(n))$$

reflecting the mean angle between the surface normal at surface point p with a neighbourhood set N and the normals at the neighbouring surface points n.

Relatively little research has been done on the connection between the shape of the cartilage and disease progression. The bio-mechanics of the joint both affect and are affected by the shape. There is also a dual connection with the structure of the underlying bone. The shape of the cartilage affects the strain on the bone and the shape of the bone caused by bone remodelling is directly reflected in the shape of the cartilage. The term 'tension' used herein is inspired by the strain that a deformable plate experiences when being bent. Here, the tension is the cumulative curvature across the plate.

Without being bound by the theory, our explanation of the success of curvature measurement in discriminating between healthy patients and those with early stage osteoarthritis is as follows. Osteoarthritis affects both the articular cartilage and the underlying bone. We show herein that the local bending (or curvedness) of the articular cartilage surface can be used as an OA progression biomarker. We use the term "Cartilage Curvature" for a summation of the local bending across the cartilage sheet into a single number.

We have demonstrated this by a specific method for computing the Cartilage Curvature in the medial compartment of the tibial cartilage sheet in knees and evaluated it for a population including both healthy subjects and subject with varying degree of OA.

The concepts are general and applicable to any cartilage surface in any joint. They can also be used on the bottom cartilage surface (facing the bone) or on the bone surface (facing the cartilage). They can also be applied to a 'virtual surface' mapped between and reflecting the shapes of the opposed exterior surfaces of the cartilage. The concepts can also be used on any explicit or implicit model representing the bone or the cartilage sheet irrespective of whether the model represents the surfaces or the interior of the anatomical objects.

We compute the cartilage bending locally by approximation of the curvature locally across the cartilage sheet and combining this curvature map into a single curvature number by computing the mean across the load-bearing area. The concepts are also applicable for any other extraction or combination of the local curvature map into a single or more numbers using for instance a mean, a summation or a weighted mean. The concepts are also applicable for combining the local curvature across the entire cartilage sheet or for using specific regions of interest.

We approximate the local curvature by measuring differences in the normal orientation of a surface model of the cartilage sheet. The cartilage bending could also be computed in a number of other ways, for instance:

The local curvatures could be approximated directly from surface point sets.

The local curvatures could be estimated from the thickness variations of the cartilage.

The local curvature could be approximated from the boundary point locations.

The local bending could be extracted from any parametric representation of the local cartilage surface.

The local curvature could be approximated from an implicit representation of the knee volume like for instance a level set representation of the cartilage sheet.

The local curvature could be approximated directly from the original scan intensities using differential geometry on iso-intensity surfaces.

The local bending could be approximated from a medial model (like the m-rep) of the skeleton of the cartilage sheet focusing on the bending of the sheet overall and not the bending of the surface of the sheet.

Bending measures could be computed using geometric flows or morphological operations or any filtering approach on either a volumetric cartilage model or directly from the original scan.

Bending measures could be computed from other data acquisition modalities such as CT, ultrasound or even reflection of laser light from the cartilage surface acquired using arthroscopy.

Although the invention has principally been defined as a method of extracting significant information from a digital image, it is of course equally applicable as an instruction set for a computer for carrying out a said method or as a suitably programmed computer.

The comparison step is preferably conducted making use of previous measurements on a healthy or diseased population of reference joints for which values or average values are stored in a database or memory location in such a computer. The computer may be programmed to display the results of the comparison as a read out.

The invention will be further described and illustrated with reference to specific embodiments thereof with reference being made to the accompanying drawings, in which.

Figure 8:
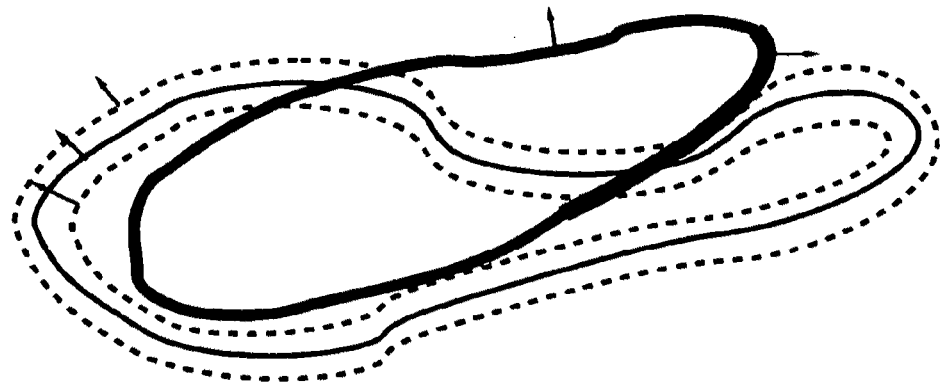
Figure 9:
Figure 10:
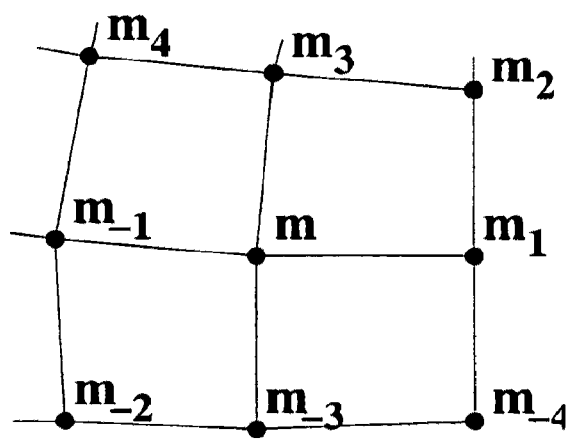
Figure 11:
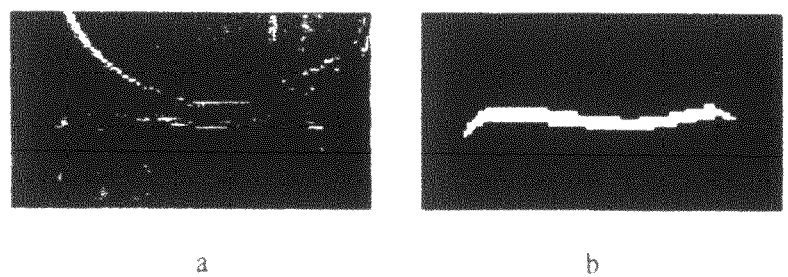
Figure 12:
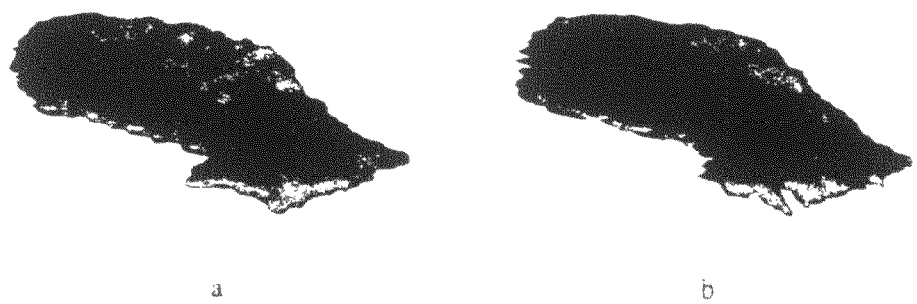
Figure 13:
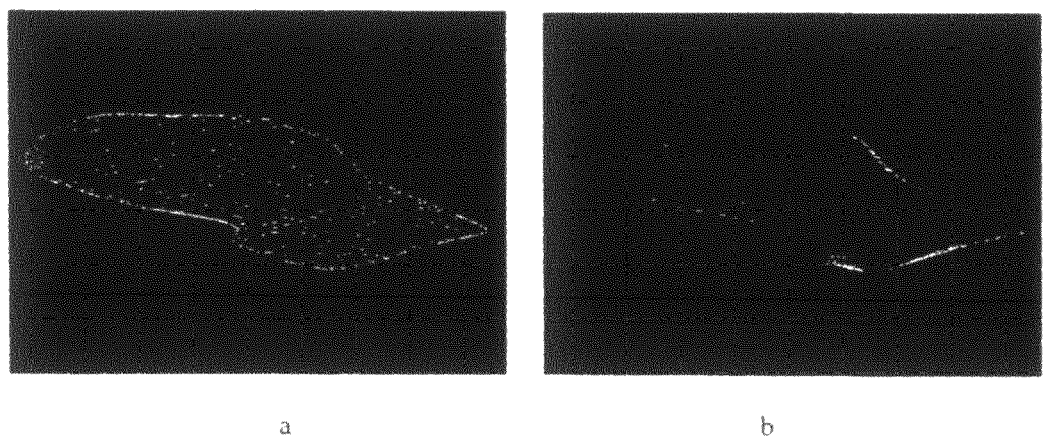
Figure 14:
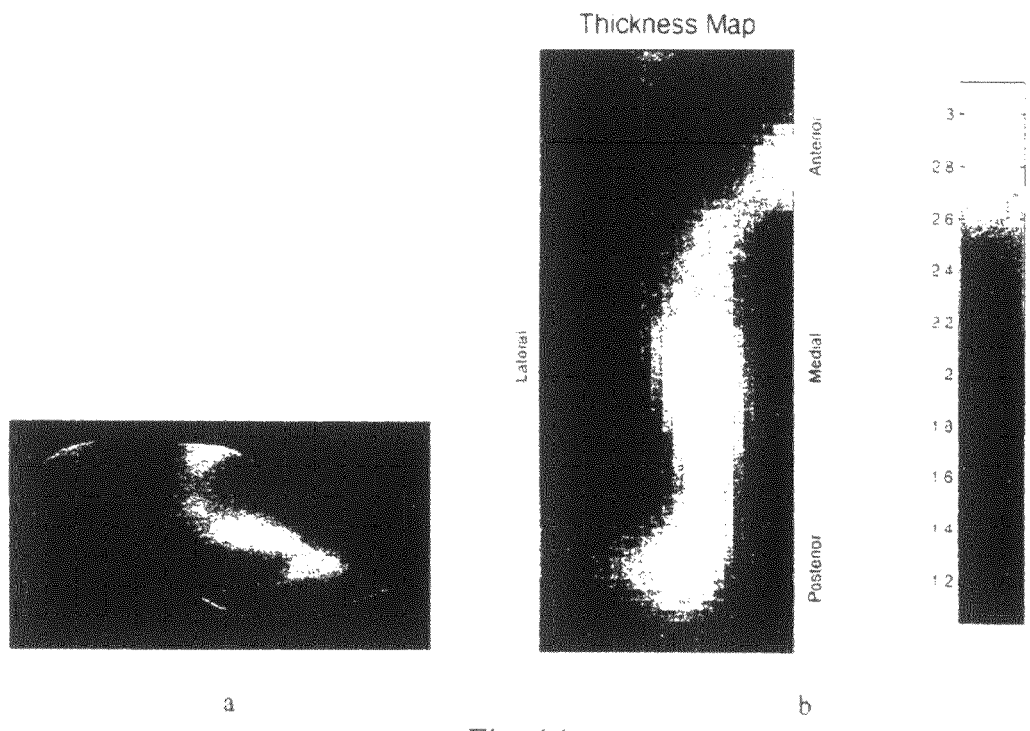
Figure 15:
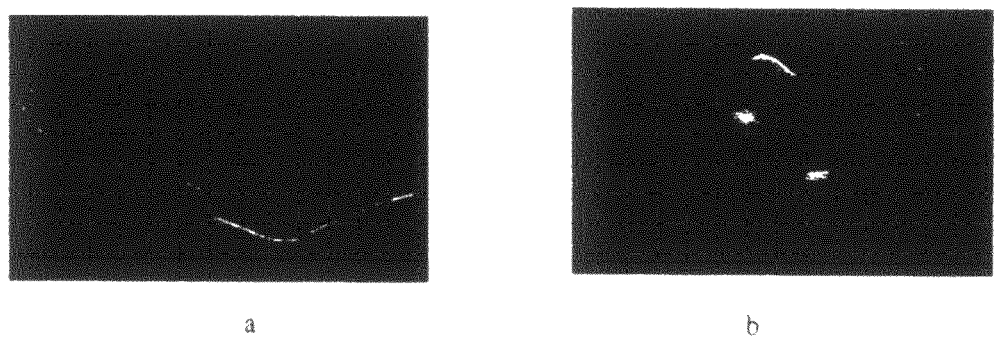
Figure 16:
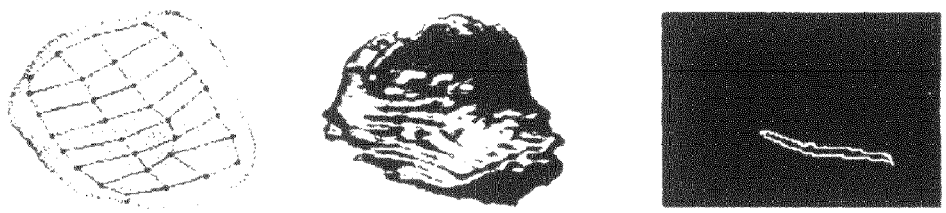
Figure 17:
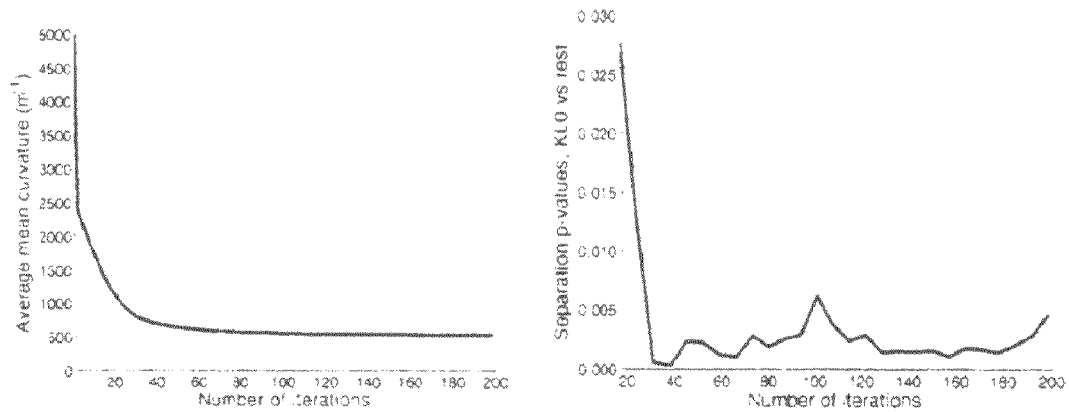
Figure 18:
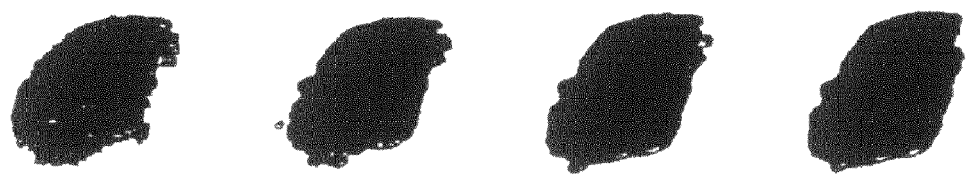
Figure 19:
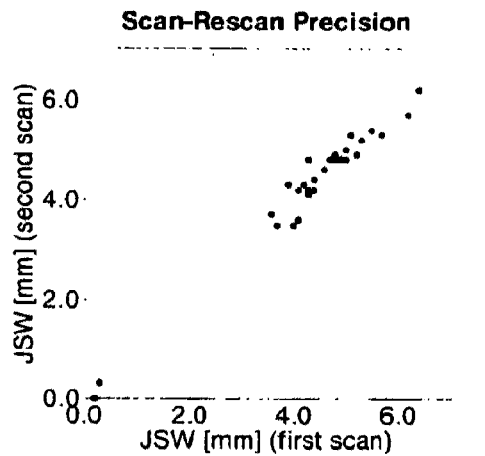
Figure 19:
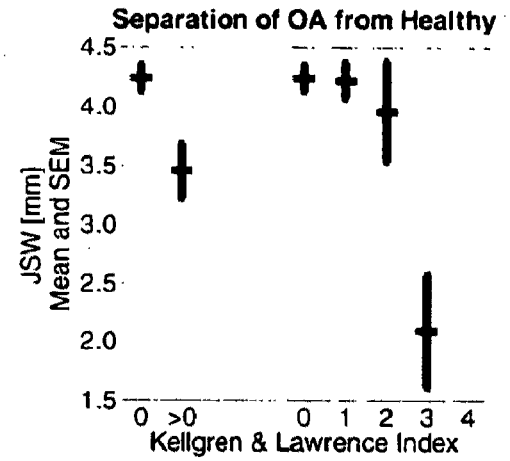
Figure 20:
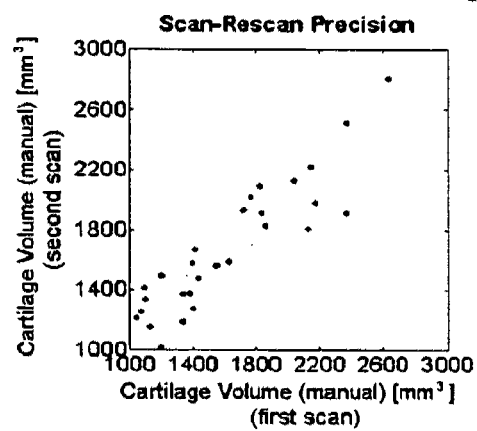
Figure 20:
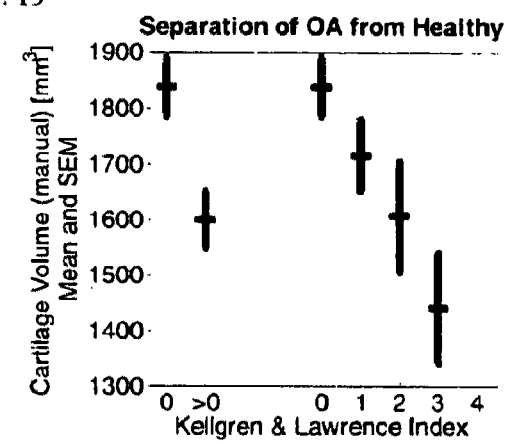
Figure 21:
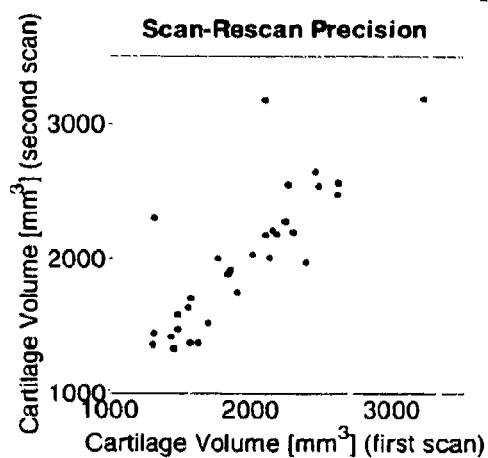
Figure 21:
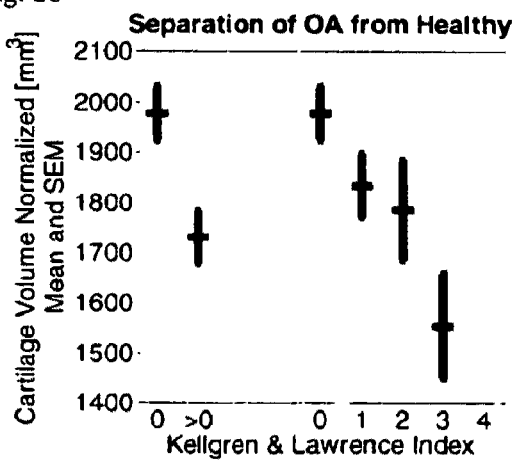
Figure 22:
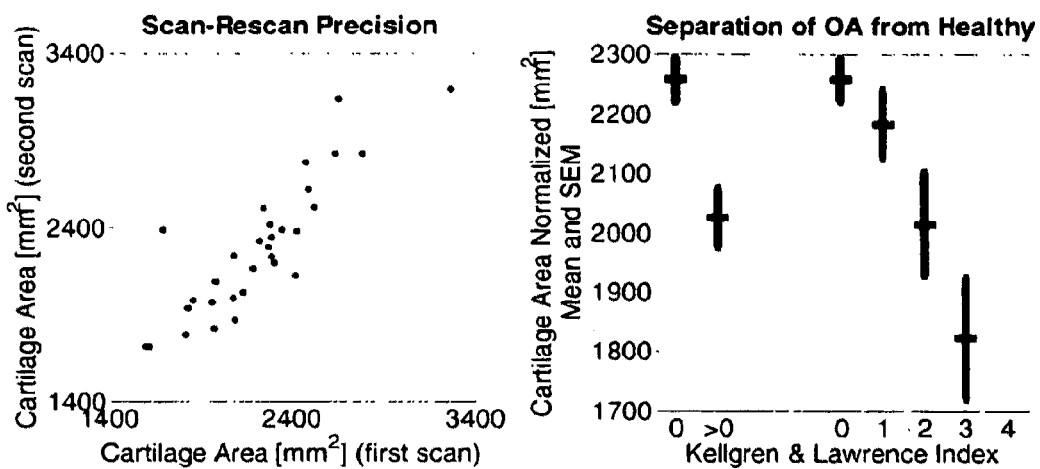
Figure 23:
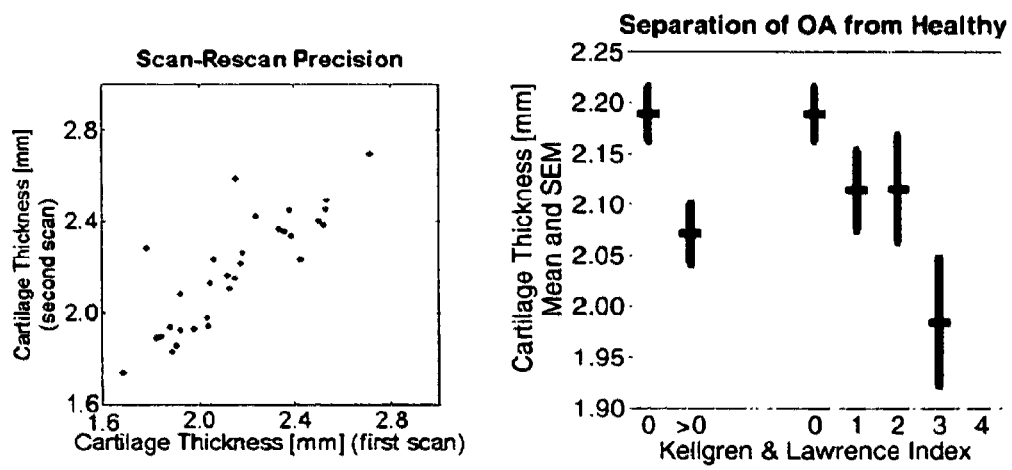
Figure 24:
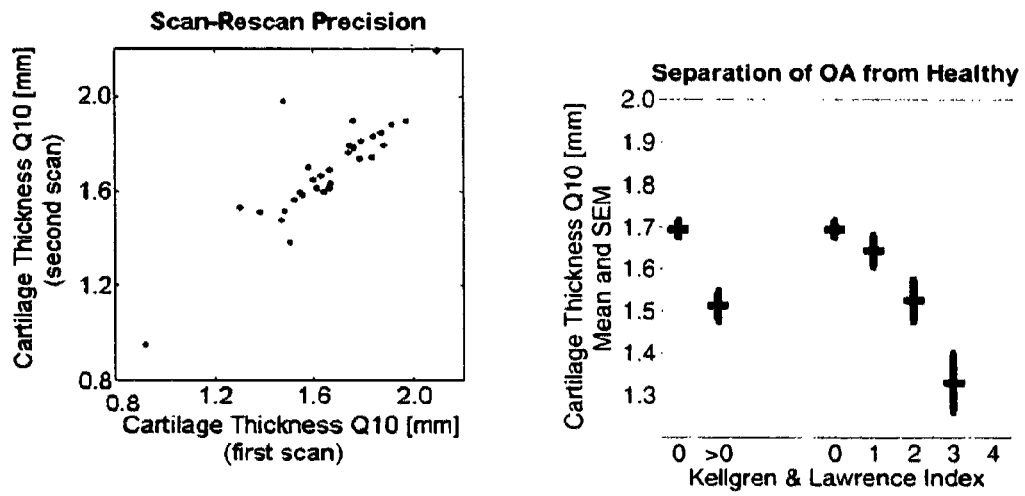
Figure 25:
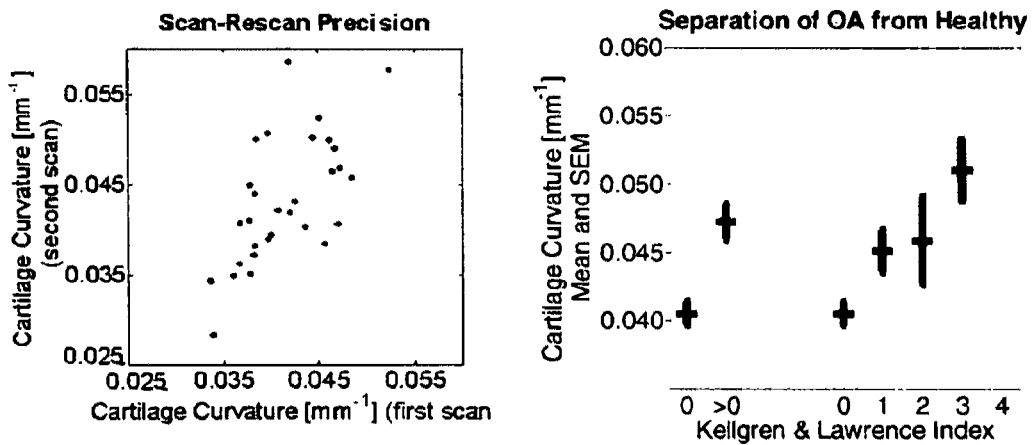

FIG. 8 shows how the image match at a model boundary point is computed as the distance to the shape boundary. The desired shape is shown in thin gray with dotted iso-distance curves. The model boundary is shown in black with the region seeking across in thick black;

FIG. 9 illustrates the process of deforming a model boundary to match an image boundary by the use of a crawl function;

FIG. 10 illustrates neighbour relationships between medial atoms, discussed below in relation to shape modelling;

FIG. 11 shows (a) sagittal slice from an MR scan and (b) the corresponding gold standard segmentation resulting from a radiologist outlining in that slice;

FIG. 12 shows visualisations in 3D of (a) a manual segmentation of an MRI of the medial compartment of a tibial cartilage and (b) a corresponding automatic segmentation;

FIG. 13 shows a shape model fitted to the automatic segmentation of FIG. 12 (b) in wire frame (a) and surface filled (b) representations;

FIG. 14 shows thickness maps of the shape model of FIG. 13, (a) as a shaded 3D representation and (b) extracted to a regular grid with the intensity map corresponding to thickness between 1 and 3 mm cartilage;

FIG. 15 shows local curvature maps derived from the model of FIG. 13, (a) of the whole in a 3D representation and (b) similarly but with only a selected region of interest shown;

FIG. 16 shows (a) an m-rep surface of a tibial medial cartilage sheet, (b) the segmented cartilage the m-rep was fitted to, and (c) part of a sagittal slice with the tibial medial cartilage delineated to the right;

FIG. 17 shows (a) the average mean curvature of the articular surface over a number of iterations, and (b) p-values from t-tests between healthy and OA groups;

FIG. 18 shows the appearance of a cartilage sheet during mean curvature flow after (a) 0, (b) 35, (c) 100 and (d) 200 iterations;

FIG. 19 shows (a) correlations between narrowest joint gap measurements derived automatically from scans made at a one week separation, and (b) comparison of healthy and OA values for joint separation;

FIG. 20 shows (a) correlations between cartilage volume measurements derived automatically from scans made at a one week separation (manual segmentation), and (b) comparison of healthy and OA values for cartilage volume;

FIG. 21 shows (a) correlations between cartilage volume measurements derived automatically from scans made at a one week separation (automatic segmentation), and (b) comparison of healthy and OA values for cartilage volume;

FIG. 22 shows (a) correlations between cartilage surface area measurements derived automatically from scans made at a one week separation, and (b) comparison of healthy and OA values for cartilage surface area;

FIG. 23 shows (a) correlations between cartilage thickness measurements derived automatically from scans made at a one week separation, and (b) comparison of healthy and OA values for cartilage thickness;

FIG. 24 shows (a) correlations between cartilage thickness Q10 measurements derived automatically from scans made at a one week separation, and (b) comparison of healthy and OA values for cartilage thickness;

FIG. 25 shows (a) correlations between cartilage curvature measurements derived automatically from scans made at a one week separation, and (b) comparison of healthy and OA values for cartilage curvature;

We shall describe a specific embodiment of the invention starting from the taking of MRI scans of knees and working through the steps of voxel classification, shape model fitting and quantification of diagnostic parameters.

An Esaote C-Span low-field 0.18 T scanner dedicated to imaging of extremities was used to acquire Turbo 3D T1 scans (40° flip angle, $T_R$ 50 ms, $T_E$ 16 ms). The scans were made through the sagittal plane with a voxel size in the range $0.7031 \times 0.70.31 \times (0.7031/0.7813/0.8594)$ mm$^3$. For this first study focusing on segmentation, a total of 71 scans were used. Among these, 50 had the resolution $0.7031 \times 0.7031 \times 0.7813$ mm$^3$, 3 the resolution $0.7031 \times 0.7031 \times 0.7031$ mm$^3$ and the remaining 18 scans had the resolution $0.7031 \times 0.7031 \times 0.8594$ mm$^3$. The scans all had the size $256 \times 256 \times 104$ voxels, but we only used the central $170 \times 170 \times 104$ voxels because only they contained information.

For comparative purposes, the scans were manually segmented on a slice-by-slice basis by radiologists. A scan slice with the tibial and femoral medial cartilage manually segmented is shown in FIG. 1a. FIG. 1b shows the same image segmented automatically as described in detail below. The sensitivity and specificity for this scan are 92.52% and 99.82% respectively, with a dice similarity coefficient of 0.83.

We examine 139 knee joints in vivo, of which 59% are from female test subjects. The ages of the test subjects varies between 22-79 years with an average age of 56 years. There are both healthy and osteoarthritic knees, diagnosed by radiologists as being between 0 and 3 on the Kellgren and Lawrence Index (Kellgren & Lawrence 1957). Specifically, of the 139 knee joints, 51 knees have KLi=0, 28 have KLi=1, 13 have KLi=2 and the remaining 22 knees have KLi=3. The scans include both left and right knees. In order to treat all scans analogously, the right knees are reflected about the centre in the sagittal plane. Of the 139 knees, 31 were re-scanned after approximately one week in order to examine the segmentation precision.

For each test subject, digital x-rays of both knees were acquired. The subject was positioned standing in a weight bearing position with the knees slightly flexed and the feet rotated externally. In order to optimise reproducibility, we used the SynaFlex (developed by Synarc) to fix the orientation for the feet and flexing of the knees.

Focus film distance was 11.0 m, and the tube was angulated in 10 degrees. Radiographs were acquired in the posterior-anterior (PA) position, while the central beam was displayed directly to the mid point of the line passing through both popliteal regions. Radiographs of both knees were acquired simultaneously.

For the segmentation of cartilage we use an approximate kNN classifier, which is implemented in an ANN (Approximate Nearest Neighbour) framework and developed by Mount and colleagues (Arya et al, 1994). The ANN classifier is in principle the same as a kNN classifier, but with the modification that one can allow for a small amount of error in the search for nearest neighbours which may improve the run time significantly. An error bound, $\epsilon$, is introduced, so instead of returning the k nearest neighbours from a data set, the ANN search algorithm returns k points such that the ratio of the distance between the ith reported point ($1 \leq i \leq k$) and the true ith nearest neighbour is at most $1+\epsilon$. We have found empirically that examining the 100 nearest neighbours yields a good balance between computational complexity and accuracy, and we set $\epsilon=2$, a value that only marginally lowers the accuracy while reducing computational time significantly.

Here, we examine the medial cartilage since OA is more often observed in this compartment (Dunn et al, 2004) and in particular in the medial tibial part (Kamibayashi et al, 1995), thus these compartments are of major interest when it comes to finding disease markers for OA. In order to separate different types of cartilage from one another we use a three class classifier, where the classes are tibial medial cartilage, femoral medial cartilage and background.

The classification is hierarchical, and the first step in a fully, automatic, morphometric quantification framework is voxel classification based on supervised learning. The local appearance of each voxel is described by differential geometric expressions based on Gaussian derivatives up to the third order (in terms of "edgeness", "flatness", orientation, "ridgeness", etc). These features are combined with intensity and position into a feature vector that represents the voxel. All features except position are measured at three scales. This gives a feature vector with 39 measurements for each voxel.

Figure 2:
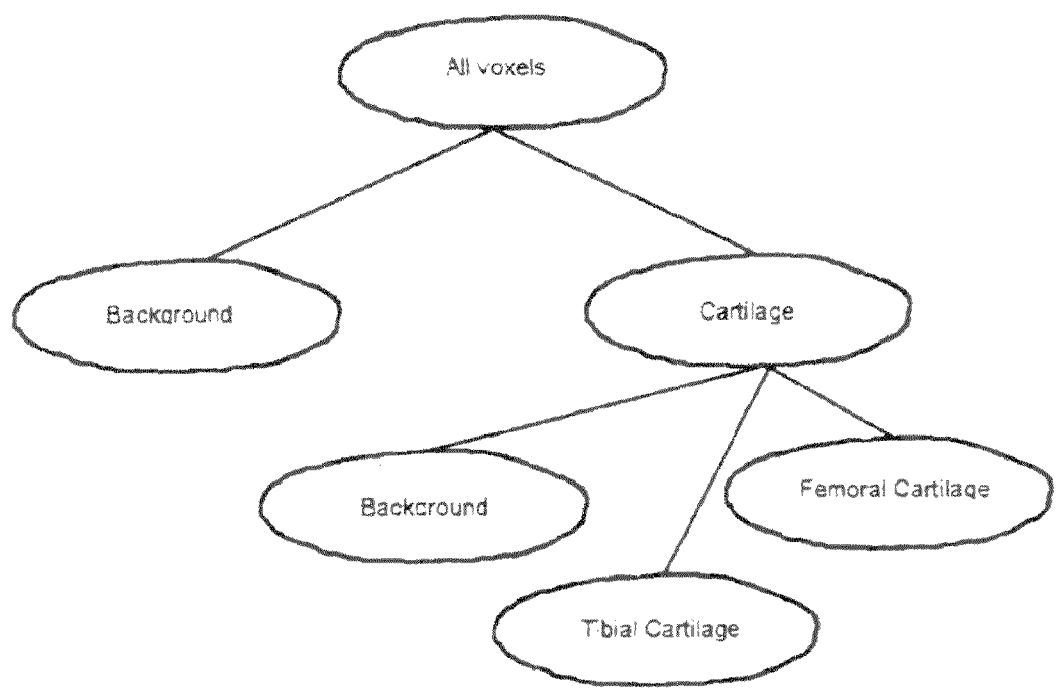
FIG. 2 shows a sketch of the hierarchical classification scheme used in segmentation of the above images.

The kNN produces class probabilities for every voxel, and in this step we set the threshold at 0.65 yielding a sensitivity for medial cartilage close to 99%. This also results in a large amount of false positives, but since typically only a few percent of the total volume within the knee belongs to the cartilage, this first step is a way of reducing data significantly. In the second step, the voxels classified as cartilage in the first step are reconsidered. This time we use a three class classifier, where the three classes are tibial and femoral medial cartilage and background, and class membership is decided based on a majority vote. The three class classifier contains more features and the features are optimized to separate the three classes whereas the classifier in the first step has features optimized to separate cartilage from background. A sketch of the hierarchical classification scheme is illustrated in FIG. 2.

Alternatively, we can use a combination of two one-versus-all classifiers, where one binary classifier is trained to separate tibial cartilage from the rest and one is trained to separate femoral cartilage from the rest, and these classifiers are combined with a rejection threshold. A voxel is classified as belonging to one cartilage class if the posterior probability for this is higher than for the other cartilage class and higher than the rejection threshold, $$j \in \begin{cases} \omega_{tm}, & P_{tm \cdot j} > P_{fm \cdot j} \text{ and } P_{tm \cdot j} > T: \\ \omega_{fm}, & P_{fm \cdot j} > P_{tm \cdot j} \text{ and } P_{fm \cdot j} > T: \\ \omega_b, & \text{otherwise,} \end{cases}$$

where a voxel is denoted j and belongs to class $\omega_i$. (tm and fm is tibial and femoral medial cartilage and b is background). The rejection threshold, T, is optimised to maximise the Dice Similarity Coefficient (DSC) between manual and automatic segmentations.

We have also tested a direct partitioning into the three classes, but the hierarchical approach yields better results and is faster, since the first step has less features and thus lower computational complexity. The classifier in the first step has a set of 33 features compared to the three class classifier in the second step that contains 51 features.

In order to find a feature set that performs well for our classification scheme, we here introduce our set of candidate features and the subsets of the features that were found from our feature selection method, which consists of sequential forward selection followed by sequential backward selection.

When a radiologist examines an MR scan for cartilage, she or he takes the location and the intensity in the image into consideration. We therefore consider these as candidate features.

One can also consider features that are related to the geometry of the object in question. The 3-jet, which is all first, second and third order derivatives with respect to (x,y,z) forms a basis which can describe all geometric features up to third order and are listed as candidate features. All the derivatives mentioned in this section are Gaussian derivatives and are defined as $$I_{i_1}, \ldots, i_n = \int \tilde{I}(\overline{x}) D_{i_1}, \ldots, i_n g(\overline{x}, \sigma_1) d\overline{x}$$

where g is a Gaussian, D a differential operator and $\sigma_1$ is the scale.

Cartilage can be described as a thin curved disc in 3D. The Hessian (H), which is the symmetric matrix containing second order derivatives with respect to the coordinates (x,y,z), $$H = \begin{pmatrix} I_{xx} & I_{xy} & I_{xz} \\ I_{yx} & I_{yy} & I_{yz} \\ I_{zx} & I_{zy} & I_{zz} \end{pmatrix}$$

is therefore considered. The eigenvectors of the Hessian point in the directions of the principal curvatures and its eigenvalues correspond to the curvature in those directions. A thin disc such as cartilage will locally yield one large and two small eigenvalues. The eigenvalues as well as the three eigenvectors are candidate features.

A feature that has been shown to be significant in the detection of thin structures such as fingerprints is the structure tensor (ST). It is a symmetric matrix containing products of the first order derivatives convolved with a Gaussian, $$ST = G_{\sigma_2} * \begin{pmatrix} I_x I_x & I_x I_y & I_x I_z \\ I_y I_x & I_y I_y & I_y I_z \\ I_z I_x & I_z I_y & I_z I_z \end{pmatrix}$$

where $\sigma$ is not necessarily the same scale as the one used for obtaining the derivatives. The ST examines the local gradient distribution at each location (x,y,z). The directions of the eigenvectors depend on the variation in the neighbourhood. The eigenvalues and eigenvectors of the ST were considered as potential features with a combination of three scales of $\sigma_1$ and three scales of $\sigma_2$.

The third order derivatives with respect to (x,y,z) can be conveniently represented in the third order tensor $I_{ijk}$. Examining the third order structure in the local gradient direction $(I_x, I_y, I_z)$ can be described using Einstein summation as $$L_{wwww} = I_{ijk} I_i I_j I_k / (I_l I_l)^{3/2}$$

The third order tensor is examined in the gradient direction on three different scales, which were considered as possible features.

The features used in the two class classifier are the position in the image, the Gaussian smoothed intensities on three different scales (0.65 mm, 1.1 mm, 2.5 mm) and the raw intensities, the first order Gaussian derivatives on scales 0.65 mm and 2.5 mm, the eigenvalues and the eigenvector corresponding to the largest eigenvalue of the structure tensor with $\sigma_1 = 0.65$ mm and $\sigma_2 = 2.5$ mm, and the eigenvalues of the Hessian on scales 1.1 mm and 2.5 mm.

The features selected as most significant are the Hessian and the structure tensor along with the intensity and the position in the image. The features were normalized between zero and one. Normalization for unit variance was also examined, but the normalization of values between zero and one produces slightly better results.

From our data set of 139 scans we use 25 for training the classifiers. Feature selection is used, which is sequential forward selection followed by sequential backward selection with the area under the ROC curve as criterion function. The selected features are: the image intensities smoothed (Gaussian) on three different scales, the position in the image, eigenvalues and the eigenvector corresponding to the largest eigenvalue of the structure tensor and the Hessian, and Gaussian derivatives up to third order. These features are ordered in decreasing significance determined by the feature selection.

The placement of the knee varies slightly in clinical studies but is still a strong cue to the location of cartilage, which will be evident in the segmentation method described below, where the position in the scan is selected as one of the most significant features. Even though the global location is a strong cue the minor variation in placement is a source of errors. Segmentation methods that rely on manual interaction are usually less sensitive to knee placement. However, in an automatic system, it is desirable to eliminate manual labour in segmentation tasks and accordingly, placement variation is an issue that needs attention.

Figure 3:
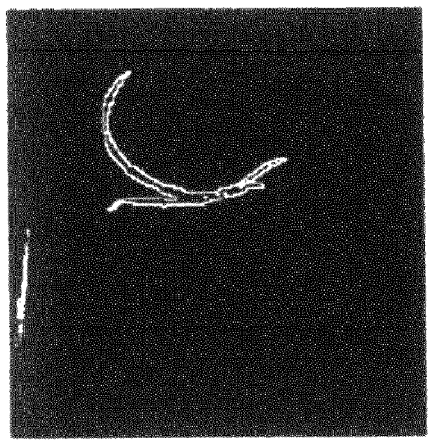
FIG. 3 shows a scan and corresponding segmented image most improved by position correction.
Figure 3:
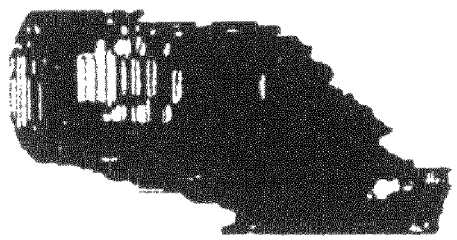
Figure 3:
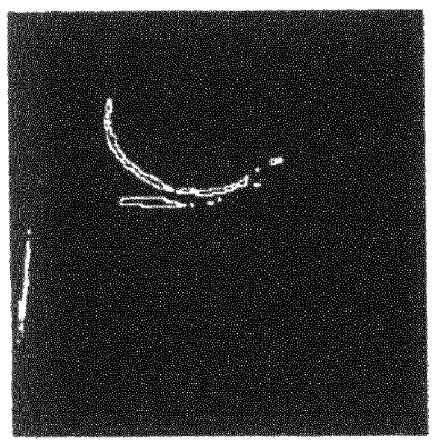
Figure 3:
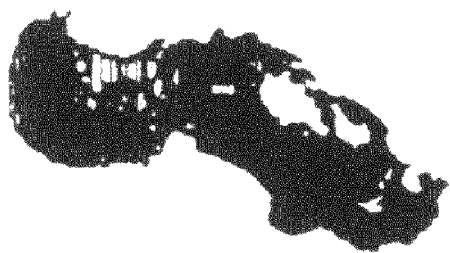
Figure 3:
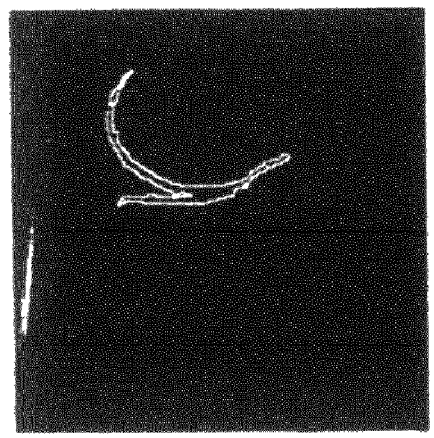
Figure 3:

FIG. 3 provides an illustration of how knee position in a scan can affect an automatic segmentation method. One way of correcting for knee placement is to manually determine where in the scan the cartilage is, but this can take time with 3D images since a human expert typically searches through the scans on a slice-by-slice basis. When the segmentation method itself is automatic, an automatic adjustment is preferred.

In order to adjust the segmentation method to become more robust to variations in knee placement, an iterative scheme, consisting of two steps, has been developed. First, the coordinates of the scan are shifted so that the cartilage centre of mass found from the segmentation is positioned at the location of the centre of mass for the cartilage points in the training set. Then the dilated volume of the segmentation is classified with the other features unchanged. The dilation extends the boundary outwards by three voxels and all voxels inside this extended boundary are reclassified. This is typically only a few percent of the total scan volume, and as a result, the computation time is not significantly increased. In order to determine if the selected region is a reasonable choice the classification is repeated with all the voxels in the image, yielding the same results with much longer computation time. The outcome is combined and the largest connect component is selected as the cartilage segmentation.

The methods are trained on 25 scans and evaluated on 114 scans. Of the 114, 31 knees have been re-scanned and the reproducibility is evaluated by comparing the first and second scanning.

The automatic segmentation yields an average sensitivity, specificity and DSC are 81.15 (+/−11.0% s.d), 99.9% (+/−0.04% s.d) and 0.79 (+/−0.07 s.d) respectively in comparison with manual segmentations. As to inter-scan reproducibility of the volumes from the automatic segmentations, the linear correlation coefficient between the first and second scanning is 0.86 for the 31 knees, with an average volume difference of 9.3%.

The fully automatic segmentation requires 10 minutes of computation (on a standard 2.8 GHz desktop computer) using an optimised algorithm for voxel classification. The segmentation mean accuracy is evaluated to sensitivity 84.2% and specificity 99.9%.

After applying position normalisation, the average sensitivity, specificity and DSC are 83.9% (+/−8.37 s.d), 99.9% (+/−0.04% s.d) and 0.80 (+/−0.06% s.d) respectively and it converges in only one iteration. Compared to the initial segmentation there is a significant increase in sensitivity ($p<1.0*10^{-7}$) and in DSC ($p<2.5*10^{-3}$) according to a students t-test. In order to illustrate how the segmentations are affected, the best results shown in FIG. 3 are compared with the worst results from the position correction scheme shown in FIG. 4. In the best case the DSC increases with 0.17 and for the worst scan it decreases with 0.017.

FIG. 3 shows the scan most improved by the position correction scheme, where the DSC increases from 0.61 to 0.77. FIG. 3(a) shows the manual segmentation, (b) shows the original segmentation and (c) shows the segmentation after position correction. The 3D views are seen from above, and the 2D images are a sagittal slice of the segmentation.

Figure 4:
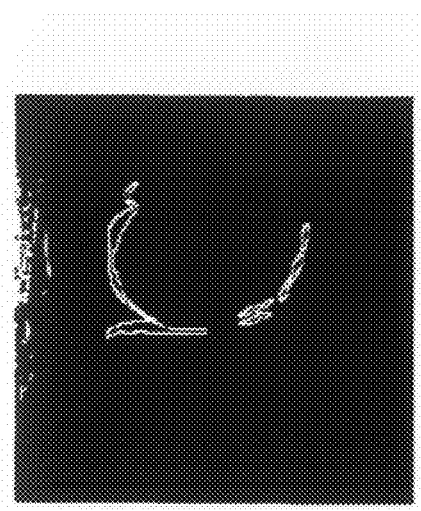
FIG. 4 shows a scan and corresponding segmented image illustrating the worst case scenario of position correction.
Figure 4:
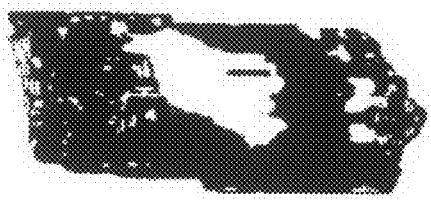
Figure 4:
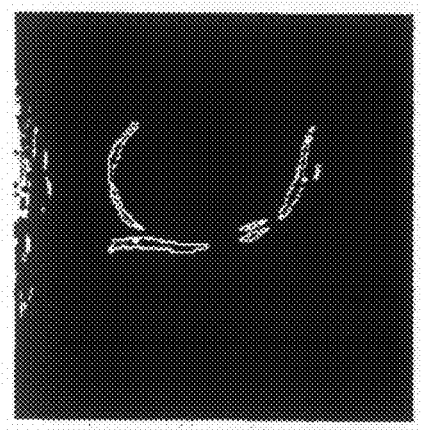
Figure 4:
Figure 4:
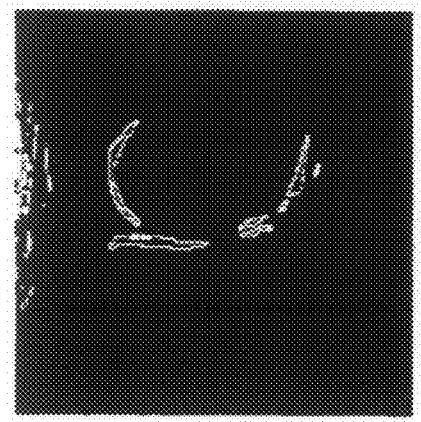
Figure 4:
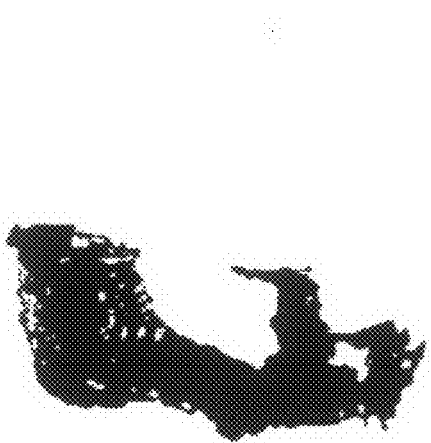

FIG. 4 shows the worst case scenario of applying position correction where the knee is severely osteoarthritic (KLi=3). For this scan there is no improvement in DSC. The manual segmentation is shown in (a), (b) shows the initial segmentation and (c) shows the segmentation after position correction.

The reproducibility of the segmentation is improved with an increase of the linear correlation coefficient from 0.86 to 0.93 and the average volume difference decreases from 9.3% to 6.2%. These reproducibility values can be compared to the volumes from the manual segmentations by a radiologist for the same data set. The linear correlation coefficient is 0.95, and the radiologist has an average volume difference of 6.8%.

The radiologist re-delineated the tibial medial cartilage in 31 scans in order to determine intra-rater variability for the manual segmentations. The average DSC between the two manual segmentations is 0.86, which explains the fairly low values of the DSC in our evaluation because the method is trained on manual segmentations by the expert and therefore attempts to mimic the expert, and assuming most misclassifications occur at boundaries, thin structures would typically have lower DSC. The corresponding DSC of the automatic segmentation versus expert for the tibial cartilage of the 31 scans is 0.82.

Figure 5:
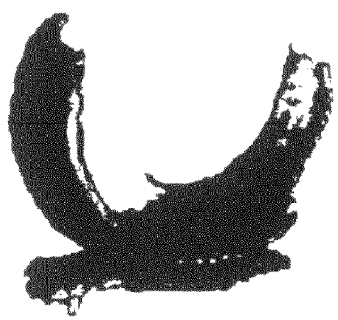
FIG. 5 shows a three dimensional surface rendering of a manual segmentation of the tibial and femoral cartilage sheets from the scan data.
Figure 6:
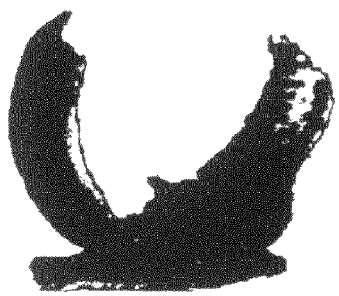
FIG. 6 shows a similar three dimensional surface rendering of a automatic segmentation of the tibial and femoral cartilage sheets from the scan data.

The results of our automatic segmentation are compared to the manual segmentation made by radiologists, resulting in an average sensitivity and specificity of 90.0% and 99.8% respectively for the test set for the medial cartilage compartments. A comparison between a gold standard segmentation and an automatically segmented knee MR scan can be seen in FIG. 5 and FIG. 6. In FIG. 5 is the manually segmented medial cartilage from a knee MR scan and in FIG. 6 the corresponding automatic segmentation. For this scan, the sensitivity and specificity are 94.82% and 99.79% respectively, with a dice of 0.81. A slice by slice comparison is displayed in FIG. 1. The dice similarity coefficient (DSC) measures spatial volume overlap between two segmentations, A and B, and is defined as $$DSC(A, B) = \frac{2 \times |A \cap B|}{|A| + |B|}$$

The Dice similarity coefficient between our automatic segmentation and the gold standard segmentation is for the test set on average 0.80.

Comparing our segmentation method with a competing semi-automatic segmentation algorithm (Pakin et al. 2002), we get a distinctly higher sensitivity and a slightly better specificity. Our segmentation algorithm performs well compared to two leading cartilage segmentation schemes, which demonstrates that fully automatic cartilage segmentation is achievable in low-field MR scanners.

The next step is to apply shape modelling techniques to the segmented image so that quantitative morphometric measures can be derived from it.

Methods based on analysis of shape variation allow statistical modelling of prior shape knowledge in tasks where the image information itself often is not strong enough to solve the task automatically. The obvious example is the use of deformable models in segmentation, where the preferred deformations are determined by a statistical shape model. A shape model is a parametric shape representation with pre-defined rules for deformation that allows the model to represent the class of shapes encountered. In medical image analysis the shape classes are typically defined by shapes of organs or other anatomical structures.

A large class of statistical shape models consist of models based on a mean shape with deformations. The mean and the corresponding deformations are constructed through statistical analysis of shapes from a collection of training data. Each shape in the training set is represented by the chosen shape representation, and analysis of the parameters for the representation give the mean and variations. The best known shape model from this class is the *Active Shape Model* (Cootes, Taylor, Cooper & Graham 1995). Here, the shapes are represented by a point distribution model (PDM) with given point-wise correspondence. The mean model is achieved after Procrustes alignment of the shapes followed by trivial mean computation of each point in the model. Principal Component Analysis (PCA) is used to provide the variations. PCA is only valid for Euclidean parameter spaces and is restricted to producing linear shape variations. Other approaches allow more complex shape variations through the use of kernel based methods (Cremers, Kohlberger & Schnörr 2002).

We have employed a medial shape representation in the form known as the M-rep (Pizer, Fritsch, Yushkevich, Johnson & Chaney 1996). This representation offers an intuitive visualization of the shape by means of the sheet of sampled medial atoms. Compared to PDM's this representation is less simple since the parameter space is not Euclidean but consists of a combination of position, scaling, and orientation parameters. Standard PCA is therefore not applicable. However, the analogue of PCA has been developed for a more general space of shape representations. This is the *Principal Geodesic Analysis* (PGA) that applies to shape representations that form Lie Groups.

A key element in constructing shape models is the representation of the shapes in the training collection. This must be done in a manner that defines/preserves correspondence across the population. For PDM's the simplest method is by manual selection of the boundary points by an expert of the specific anatomical structure. In 2D this is a time-consuming and tedious process—in 3D it is not feasible. However, this process can be automated. The approach presented by Davies, Twining, Cootes, Waterton & Taylor (2002) starts by generating boundary points from a spherical harmonics shape representation. This set of boundary points and their correspondences are then optimized through a *Minimum Description Length* (MDL) approach.

We describe here an automated shape modelling method. The core is a fully automatic bootstrap process that iteratively optimizes the shape model on a training collection and then derives the PGA mean and modes of deformation. Through the bootstrap iterations, the PGA mean converges to an (optimal) shape mean for the collection. The PGA modes of variation converge and give the modes of variation for the shape model.

The flavour of this work resembles the MDL method in Davies et al. (2002). The main difference—apart from the shape representation—is that the MDL approach starts the optimization process from shape representations with good training shape fit and poor correspondence. The MDL process then keeps the shape fits while optimizing the correspondence. The PGA bootstrap starts from a generative model with explicit correspondence but with poor fit to the individual training shapes. The bootstrap process then keeps the correspondence while optimizing the fit to the training shapes.

We here evaluate the PGA bootstrap method for constructing shape a model for the collection of medial tibial cartilage sheets mentioned above. The shape model both allows automatic segmentation and defining of the correspondence needed for focal measures such as thickness.

When building a shape model, the task is to construct a compact description of a distribution of shapes observed through a training collection. This allows generation of plausible shapes and analysis of existing shapes. The task at hand determines which aspects of shape to model. Here, we focus on the "overall shape". This means that the fine scale details are ignored and that we seek a compact representation of smooth shapes. Since we seek a model of smooth shapes, we aim for a smooth representation of the training shapes.

We use a medial shape representation, m-rep, as our smooth shape representation of choice. Below, we briefly review the geometry and the framework for image segmentation (Pizer, Chen, Fletcher, Fridman, Fritsch, Gash, Glotzer, Jiroutek, Joshi, Muller, Thall, Tracton, Yushkevich & Chaney 2003, Joshi, Pizer, Fletcher, Yushkevich, Thall & Marron 2002) and introduce the image match and the regularization terms essential for the shape model building framework.

The m-rep is based on the medial axis of Blum (Blum & Nagel 1978). In this framework, a 3D geometric object is represented as a set of connected continuous medial sheets, which are formed by the centres of all spheres that are interior to the object and tangent to the object's boundary at two or more points. Here we focus on 3D objects that can be represented by a single medial sheet.

We sample the medial sheet M over a spatially regular lattice of medial atoms (see FIG. 7) defined as a 4-tuple $m=\{x,r,F,\theta\}$, consisting of: $X \in \mathbb{R}^3$ and $r \in \mathbb{R}^+$, the centre and radius of the sphere, $F \in SO(3)$ an orthonormal local frame parameterized by $(b,b^\perp,n)$, where n is the normal to the medial manifold, b is the direction in the tangent plane of the fastest narrowing of the implied boundary sections, and $\theta \in [0, \pi)$ the object angle determining the angulation of the two implied opposing boundary points to the local frame. Given an m-rep figure, we fit a smooth boundary surface to the model. We use a subdivision surface method (Thall 2002) that interpolates the boundary positions and normals implied by each atom.

The previous section describes how to derive a shape from an m-rep model. For shape model building, it is required to go the other way: from the shape to an m-rep. Since m-rep is a generative shape model, representing a shape is equivalent to segmenting the binary image corresponding to the shape.

Following the deformable models paradigm, an m-rep model M is deformed into an image I by optimizing an objective function:

$$F(M,I)=L(M,I)+\alpha G(M)+R(M)$$

The function L, the image match, measures how well the model matches the image information, while G, the geometric typicality, gives a prior on the possible variation of the geometry of the model weighted by $\alpha \geq 0$. The last term R, the model regularization, is an addition to the standard m-rep framework. As deriving an m-rep from a shape does not produce a unique answer, model regularisation may be used to select the optimum m-rep solution.

In this shape model building framework, m-rep models are fitted to the desired shapes. In previous work (Dam et al. 2004), the image match term of the objective was computed as the correlation between a Gaussian derivative kernel in the normal direction of the object at the implied boundary points. This image match term proved to be too local. In a segmentation setting including a shape model, this type of image match is often sufficient—but while building a shape model there is no prior shape model and therefore the image match needs to be able to attract the model boundary to the shape boundary even though it is far from it.

Instead we here introduce the distance from the model boundary to the shape boundary integrated over the model boundary as the basic image match function to minimize. This has some clear advantages. First, a distance transform from the shape boundary can be computed prior to model optimization and thereby ensure fast optimization. Secondly, the model can be attracted to the shape from infinitely far away.

The computation of the distance from the model boundary to the shape boundary has two special cases in order to help the optimization.

First, we use the shape boundary distance gradient and the model boundary normal to determine whether the nearest shape boundary is the correct one (as illustrated in FIG. 8). This is done to ensure convergence to the correct optimum. Otherwise the model could shrink to a single point arbitrarily located at the shape boundary and reach minimal shape match penalty. Also, it avoids faulty local minima where a part of the model boundary gets stuck at the wrong shape boundary. This is checked at the model boundary point given by the parameter s with the transition function ws (for wrong side):

$$ws(s)=\min(1,\max(0,-mbn(s) \cdot g(s)))$$

where mbn is the model boundary normal and g is the shape distance function gradient. By not normalizing the gradient, we avoid arbitrary directions given by gradients close to zero. The function gives a soft transition between 0 and 1 for model boundary point on the right vs wrong side. In FIG. 8, the image match at a model boundary point is computed as the distance to the shape boundary. The desired shape is shown in black with dotted iso-distance curves. The model boundary is shown in thin/thick lines. The gradient of the shape boundary distance function and the model boundary normals are used to ensure that the boundary point does not get attracted to the wrong boundary. Shape distance is negative inside the object, so shape distance gradient arrows in black point away from the centre of the shape. When the model normal is in opposite direction to the shape distance gradient (determined by the sign of the dot product) the boundary distance is not just the value of the shape boundary distance function but approximated by adding the maximal shape radius. This is the case for the thick part of the model boundary. The principles are identical in 3D.

Secondly, for thin shapes the central part of the model optimization is the phase where the model ends needs to crawl into the shape ends (illustrated in FIG. 9). This is problematic since the shape boundary distance function offers no help. The ends of the model is equally likely to move slightly inwards or outwards depending on the local narrowing of the thin shape and then get stuck in a local minimum.

One solution to this problem could be to let the end parts of the model be optimized by the distance to the shape boundary in a direction normal to the model (as opposed to normal to the shape boundary as described above). This will fail for special shapes (for example a constantly curving shape) and experiments on both artificial and real data also shows that the ends get stuck in local minima. Another solution is to add the distance from the model boundary to the shape boundary in a direction normal to the model boundary—integrated over the shape boundary instead of over the model boundary. This would solve the problem. However, computing distances from the model boundary is computationally costly since the model is repeatedly changed during optimization.

We add a constant expanding force to the end parts of the model boundary that are inside the shape boundary. In the optimization scheme, this simply means that the change of the image match is defined as the signed displacement in a direction normal to the model boundary. This is applied for model boundary points that are inside the shape and where the model boundary normal is approximately perpendicular to the shape boundary distance gradient. As the model crawls into the end of the shape during optimization, the boundary distance gradient becomes approximately parallel to the model boundary normal and this expanding force is cancelled.

Analogously, for model boundary points outside the shape boundary also with normal approximately perpendicular to the shape boundary distance gradient, an imploding force is added. Thereby the model boundary can also crawl into indentations in the shape.

The model boundary places where crawling is relevant are detected by the transition function crawl:

$$\text{crawl}(s) = \min\left(1, \left(\max\left(0, 2 - \frac{1}{\theta_{crawl}}\left|\text{angle}(mbn(s), g(s)) - \frac{\pi}{2}\right|\right)\right)\right)$$

The free parameter $\theta_{crawl}$ determines how close to perpendicular the model boundary and the shape boundary distance function gradient must be before crawling. The term inside |•| is an angle being zero when the model boundary normal and the shape boundary distance function gradient are perfectly perpendicular. The remaining expression ensures crawl equal 1 for this angle smaller then $\theta_{crawl}$ with a linear transition to crawl for then angle increasing to $2\theta_{crawl}$. For boundary points at the ends of the model, the shape boundary distance function offers no help for the deformation of the model. The red model boundary points with a normal approximately perpendicular to the black shape boundary distance gradient are assigned an outwards force in the optimization that allows the model to crawl into the ends of the shape. The principles are identical in 3D.

The image match term of the objective function, L, is now computed as the integral of the boundary distance, modified as described above, at each model boundary point.

$$L(M, I) = \int_{B(M)} (1 - ws(s))|\text{Dist}(s)| + ws(s)(\text{Dist}(s) + shapeDiam)\,ds$$

$$\text{Dist}(s) = (1 - \text{crawl}(s))S_{dist}(mb(s)) + \text{crawl}(s)\text{Displ}(s)$$

$$\text{Displ}(s) = -\text{sign}(S_{dist}(mb(s)))\frac{\partial mb(s)}{\partial t} \cdot mbn(s)$$

where mb is a model boundary point using some parameterization s of the model boundary B(M). $S_{dist}$ is the shape boundary distance transformation function.

As explained above, the transition function ws determines whether to use the shape boundary distance directly or to add the diameter of the shape shapeDiam (computed as twice the maximal internal shape boundary distance) and thereby go across the shape when computing the distance to the shape boundary.

And crawl determines whether crawling at the model boundary is relevant at the model boundary and thereby invokes the displacement given by Displ. The parameter t in the partial derivative on mb is a fiducial optimization evolution parameter—the term simply means that a movement in the direction of the model boundary normal is interpreted as a step towards the shape boundary. The sign of the shape distance function ensures that this term applies both for model boundary points inside the shape crawling out into extrusions and for points outside crawling into indentations.

The details make the image match function appear complicated. It is simply the distance from the model boundary to the shape boundary—just with two intuitively simple special cases that ensure that the model boundary does not get stuck on the outside shape boundary and that the model boundary is allowed to crawl into thin extrusions/indentations.

Intuitively, the geometric typicality term is a geometry prior that ensures that the model optimization favours models with a probable geometry. However, when building a shape model, no shape prior is available. Therefore the geometric typicality term, G, is defined as the change in the boundary from the previous optimization stage (where $mb_0$ is the previous boundary position):

$$G(M) = -\int_{B(M)} \frac{\|mb - mb_0\|^2}{r^2}\,ds$$

With a statistical shape model that defines global deformations by a linear combination of major modes of variation, such as the PCA model in the active shape model (or alternatively PGA modes for an m-rep framework) the term above can be supplemented by the standard Mahalanobis distance.

The model regularization term, R, corresponds in spirit to the curvature and neighbour distance terms that are present in the original active contour model (Kass, Witkin & Terzopoulos 1988) as well as contemporary implementations of shape model building frameworks based on the active shape model (Thodberg & Olafsdottir 2003, Thodberg 2003). The term is added at the atom scale level in order to keep the model "nice".

Model regularity is essential for ensuring proper correspondence across model instances. Ideally, the model regularization does not affect the geometry of the model it just dictates the choice of model parameterization among the manifold of possible models that can represent a given shape. However, due to sampling and implementation details, the model regularization will affect the resulting model geometry marginally.

For a medial atom m with neighbour atoms $m_i$ (see FIG. 7), we define the model regularization term:

$$R(m) = \gamma_{dist}\sum_{j=1}^{8} rd[d(m, m_j), \overline{d(\cdot, \cdot)}]^2 + \gamma_{curv}\sum_{i=1}^{4} \text{angle}(m - m_i, m - m_{-i})^2 +$$

$$\gamma_{orient}\left(\text{angle}(b, b_{ideal})^2 + \sum_{i=1}^{4}|\text{angle}(m_i - m_{-i}, n) - \pi/2|^2\right) +$$

$$\gamma_{boundary}\int_{B(M)}\sum_{j=1}^{8} mbn(s) \cdot mbn_j(s)$$

The first term penalizes unevenly spaced atoms weighted by the constant $\gamma_{dist}$. Here $d(\bullet,\bullet)$ is the distance between atoms, rd is the relative difference, and $\overline{d(\bullet,\bullet)}$ is the mean vertical/horizontal/diagonal distance for the model.

Figure 7:
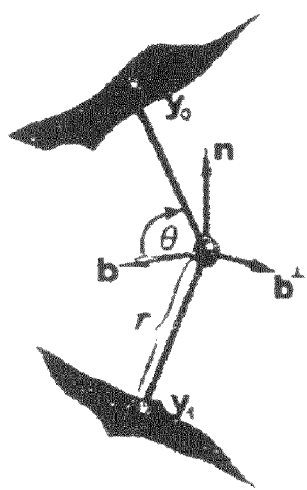
FIG. 7 illustrates the principles of producing an m-rep and shows (a) Left: Medial atom. (b) Right: Dashed grid of spherical atoms with orientation b vectors and implied boundary point vectors. The interpolated, implied boundary is illustrated by the wire-frame surface.
Figure 7:
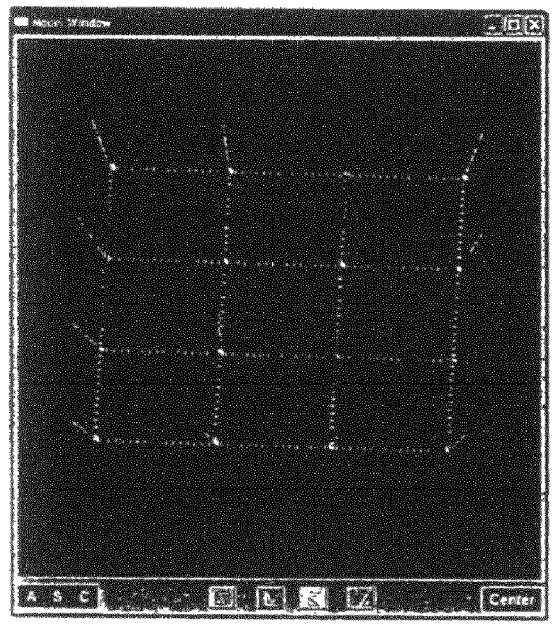

The second term penalizes high curvature and non-regular angles in the atom grid weighted by $\gamma_{curv}$. The atom $m_i$ is the neighbour opposing $m_{-i}$ (as illustrated in FIG. 7).

The term weighted by $\gamma_{orient}$ penalizes non-regular orientation of the atom coordinate frame. The first part compares the b direction with $b_{ideal}$ which is a weighted sum of the horizontal and vertical vectors between opposing neighbours across the atom. The weights are given by a linear combination of the atom coordinates scaled to between 0 and 1 such that orientation should preferably be straight away from the coordinate centre (as illustrated by the orientation vectors in FIG. 7). The second half of the term penalizes if the atom orientation normal vector n is not perpendicular to the atom grid.

The final term penalizes high curvature of the resulting model boundary weighted by $\gamma_{boundary}$. The curvature is approximated by the dot products between the boundary point normal and the neighbouring boundary point normals. As illustrated in FIG. 8, the central medial atom, m, has 8 neighbours numbered i=1.4 with opposing neighbours i=−1 . . . −4. When the relative neighbour positions are not important, we number the neighbouring atoms j=1.8.

The equations above demand some special cases for medial atoms with less than 8 neighbours at the edge of the medial sheet. The skilled person will understand how to deal with these special cases as implementation details.

Optimization of the objective function above now allows deformation of an m-rep model such that it represents a given shape. The optimization function is optimized using a multi-scale conjugate gradient method. The multi-scale element consists of optimizing with the gradient computed at successively smaller scales in order to avoid getting stuck in local minima. We start from a suitable m-rep model and then perform the following steps:

The model is translated and scaled to the centre of mass and volume of the shape.

The model is optimized at the figural level. The allowed transformations are a global similarity transform plus an elongation of the entire figure.

The model is optimized at the atom level. Each medial atom is independently transformed by a similarity transform plus a rotation of the object angle.

We apply this model fitting method using the starting model shown in FIG. 7 to represent the shapes in the training collection. For this we use the following parameters: $\alpha=1$ in the figure stage and $\alpha=0$ in the atom stage, $\theta_{crawl}=0.4$, $\gamma_{dist}=0.0001$, and $\gamma_{boundary}=\gamma_{curv}=\gamma_{orient}=0.001$. The choice of parameters are somewhat arbitrary and the result of experiments showing the suitable order of magnitude rather than specific values. The exception is the choice of $\alpha=1$ in the figure stage. For building a shape model (as opposed to performing segmentation using an existing shape model) geometric typicality does not really make sense so $\alpha=0$ would be the natural choice. However, for shapes with no natural orientation, the figure stage optimization can result in an arbitrarily oriented model. For correspondence considerations a stable model orientation is desirable and therefore $\alpha=1$ is used.

Thereby, a collection of shapes can be represented automatically by the model optimization method. In order to build a shape model, the distribution of shapes needs to be determined from the resulting collection of models. This is done below.

Principal geodesic analysis (PGA) (Fletcher, Lu & Joshi 2003) is a generalization of principal component analysis (PCA) to curved manifolds. We briefly review the results here.

As shown in (Fletcher, Lu & Joshi 2003), the set of all medial atoms forms a Lie group $M=\mathbb{R}^3 \times \mathbb{R}^3 \times SO(3') \times SO(2)$, which we call the medial group. Likewise, the set of all m-rep models containing n medial atoms forms a Lie group $M^n$, i.e., the direct product of n copies of M. This allows the definition of the exponential and logarithmic maps, $\exp(\cdot)$ and $\log(\cdot)$, that defines the geodesics of the medial group.

The Riemannian distance between m-rep models $M_1, M_2$, $\in M^n$ is given by $d(M_1, M_2) = \|\log M_1^{-1} M_2\|$ Thus, the intrinsic mean of a set of m-rep models $M_i, \ldots, M_N$, is the minimizer of the sum-of-squared geodesic distances:

$$\mu = \underset{M \in M^n}{\operatorname{argmin}} \sum_{i=1}^{n} \|\log(M_i^{-1} M)\|^2$$

Principal components of Gaussian data $\mathbb{R}^n$ are defined as the projection onto the linear subspace through the mean spanned by the eigenvectors of the covariance matrix. If we consider a general manifold, the counterpart of a line is a geodesic curve.

As shown in (Fletcher, Joshi, Lu & Pizer 2003), the covariance structure of a Gaussian distribution on 1 may be approximated by a covariance matrix $\Sigma$ in the Lie algebra $m^n$. The eigenvectors of this covariance matrix correspond via the exponential map to geodesics on $M^n$, called principal geodesics.

Algorithms for computing the m-rep mean and the principal geodesic analysis on a population of m-rep figures are given in (Fletcher, Joshi, Lu & Pizer 2003).

Analogous to linear PCA models, we may choose a subset of the principal directions $u^{(k)} \in m^n$ with corresponding variations $\lambda_k$ that is sufficient to describe the variability of the m-rep shape space. New m-rep models may be generated within this subspace of typical objects. Given a set of coefficients $\{\alpha_1, \ldots, \alpha_l\}$, we generate a new m-rep model by $M = \mu \exp(\Sigma_{k=1}^{l} \alpha_k u^{(k)})$, where $\alpha_k$ is chosen to be within $[-3\sqrt{\lambda_k}, 3\sqrt{\lambda_k}]$.

The building blocks for the shape model building framework are now ready. Using a fiducial starting model, we use the model optimization method described above to create representations of each shape in the desired training collection. Principal geodesic analysis is used to extract a mean and modes of deformation from these shape representation.

If the starting model requires much deformation in order to fit the shapes, the correspondence from shape to shape is potentially ruined. And since the fiducial starting model is by definition not designed to fit the shapes, this is a real risk. Furthermore, the resulting shape mean could have a slight bias towards the starting model.

Therefore it makes sense to redo the shape representation optimization step again—now starting from the derived shape mean instead of the fiducial starting model. And in the natural generalization, to iterate this process until the derived shape mean and modes of variation no longer change.

During these iterations, the modes of variation in the shape model are now used in the figure level deformation (and thereby adding the Mahalanobis distance to the geometric typicality term). The idea is that during the bootstrap iterations, the shape mean will converge, and that the global modes of variation will capture most of the necessary deformation such that only little deformation is needed at the atom level. This ensures both fast optimization and good correspondence in the optimized models.

From the collection of MR knee mentioned above we randomly selected a training set of 25 scans for building the shape model following the method described above. This shape model was used for representation of the automatic segmentations of cartilage sheets (obtained using the classification method described above) using the automatic shape model optimization scheme described above. This results in an m-rep model for each cartilage sheet. An example of such a deformed shape model is given in FIG. 13.

Having developed an adequate shape model and having applied this to a segmented image, one can move on to extracting quantitative data therefrom on a reproducible basis as described below.

In this study focusing on morphometric analysis of tibial cartilage, we continue to focus on the medial compartment of the tibial cartilage sheet since the correlation between degradation and clinical symptoms is predominant in the medial compartments (Dunn, Lu, Jin, Ries & Majumdar 2004) and in particular in the tibial part (Kamibayashi, Wyss, Cooke & Zee 1995).

Focus film distance was 1.0 m, and the tube was angulated in 10 degrees. Radiographs were acquired in the posterior-anterior (PA) position, while the central beam was displayed directly to the mid point of the line passing through both popliteal regions. Radiographs of both knees were acquired simultaneously.

We acquired knee MRI using an Esaote C-Span 0.18T scanner dedicated for imaging of the extremities—the same scanner mentioned previously. We used the same knee coil for all subjects. The sequence was a sagittal Turbo 3D T1 (flip angle 40°, TR 50 ms, TE 16 ms) with scan time around 10 minutes. The resolution was 0.70 mm×0.70 mm in each slice with a slice thickness between 0.70 mm and 0.93 mm but typically at 0.78 mm. See FIG. 1 for an illustration of a scan.

The articular cartilage in the medial compartment was manually segmented by slice-wise delineation by a radiologist as in FIG. 11. These manual segmentations were used for training of the automatic methods.

From the X-rays, the radiologist determined the KL score (Kellgren & Lawrence 1957) on the scale from 0 (normal) to 4 (severe OA). The score is based on a qualitative evaluation of presence of osteophytes, joint gap narrowing, and in the severe cases sclerosis of the subchondral bone.

The joint space width was measured from the X-rays by a radiologist by manually marking the narrowest gap between the femur and the tibia in the medial compartment.

The radiologist also marked the most medial and lateral points on the tibial plateau (not including possible osteophytes). These points define the tibial plateau width which we use as a simple measure of the overall size of the knee.

The first step in the fully automatic, morphometric quantification methods as described above is voxel classification based on supervised learning. (Folkesson, Dam, Olsen, Pettersen & Christiansen 2005): This step is described in detail above and briefly reviewed here.

Figure 1:
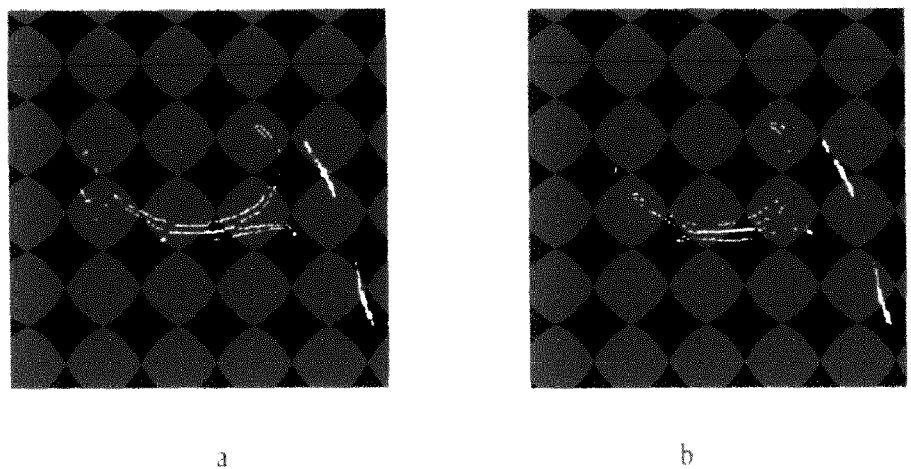
FIG. 1a shows an MRI scan slice with the manual segmentations of the tibial and femoral medial cartilage shown as superimposed outlines.
FIG. 1b shows an MRI scan slice with the automatic segmentations of the tibial and femoral medial cartilage shown as superimposed outlines.

These feature vectors from the voxels from the 25 scans in the training set form a database of examples of tibial cartilage, femoral cartilage and background voxels. The automatic segmentation on a new scan is performed by classifying each voxel using a k Nearest Neighbour classifier. Classification outliers are removed by selecting the largest connected component. During the automatic steps, right knees are mirrored around the center sagittal plane in order to manage all knees in the same framework. Visualizations in 3D of the manual (left) and corresponding automatic (right) segmentation of the medial compartment of the tibial cartilage from the scan from FIG. 1 are seen in FIG. 12.

A voxel classification does not allow morphometric quantification. In order to do that properly, a representation of the cartilage surfaces is needed. Therefore, we fit a shape model to the result of the automatic segmentation as described above.

We use a shape model, the mr-rep (Joshi, Pizer, Fletcher, Yushkevich, Thall & Marron 2002), and deform it, using the methodology described above, such that the model boundaries are aligned with the transition between cartilage and background. This is done by optimizing the parameters for the shape model such that the boundary is descending in a landscape constructed by boundary distance transformation performed on the result of the automatic segmentation. FIG. 13 shows the shape model fitted to the automatic segmentation from FIG. 12. Left: The model is shown as a wire-frame with the internal skeleton that defines the model coordinate system. Right: The model shown as a surface model.

The m-rep is a medial shape model (medial in the mathematical sense). This means that the basic atoms of the model are in the centre of the objects and have the radius as the central attribute. Thereby, the choice of shape model makes it fairly simple to extract a thickness map across the cartilage sheet—as illustrated in FIG. 14 which shows Left: Map of the local thickness across the surface of the cartilage sheet shape model from FIG. 13. Bright areas are thicker. Right: Using the coordinate system given by the shape model, this map can also be illustrated in a regular grid.

In relation to this illustration, we use the term Cartilage Thickness as the mean of the thickness map excluding the edges of the cartilage sheet (around the crest of the shape model).

Cartilage thickness is also intended to quantify cartilage loss. However, a thickness map directly allows detection of local variation and thereby analysis of whether the cartilage loss is caused by overall thinning or by focal lesions.

In order to derive a measurement of 'curvature' (see above for definition), analogous to the thickness map, we compute a surface curvature map for the cartilage sheet. The curvature is locally approximated by the change in cartilage surface normals in a small neighbourhood. The curvature map is illustrated in FIG. 15. This shows, Left: a map of the local curvature across the surface of the cartilage sheet shape model from FIG. 13. Right: Since the curvature is dominant around the crest of the shape, we define an area of interest surrounding the load-bearing area. The intensities are rescaled to reveal the areas with large surface bending as bright areas. Since the curvature of the model is dominant at the edges of the cartilage sheet (the crest of the shape model), we define an area of interest that includes the load-bearing area of the cartilage sheet but excludes the crest. This area of interest is defined in terms of the coordinate system of the shape model (illustrated in FIG. 13).

In the remainder of this discussion, we use the term Cartilage Curvature for the mean of the local curvature approximation across the load-bearing area of the cartilage sheet.

More accurately, we compute the cartilage Curvature in two steps. First a curvature map is computed across the surface of the cartilage shape model. Secondly, the cartilage curvature is computed as the mean curvature across a region of interest.

The cartilage shape model results in a surface sampling consisting of surface point with known normal directions and known coordinates. The coordinates allow specification of a local neighbourhood used for the local curvature approximation.

For a surface point p with a neighbourhood set N, the curvature is approximated as follows:

$$\text{curvature}(p) = \frac{1}{|N|} \sum_{n \in N} \arccos(\text{normal}(p) \cdot \text{normal}(n))$$

The expression is simply the mean angle between the surface normal at p and the normals at the neighbouring surface points n. Any other arithmetical manipulation of the direct value of the equation may be used.

For example, in one embodiment, we define the load bearing (central) part of the articular surface as a region of interest and estimate the curvature locally in a 5×5 neighbourhood by taking the angle between the normals and dividing it by the distance between them:

$$\text{curvature}(p) = \frac{1}{|N|} \sum_{n \in N} \frac{1}{dist(p,n)} \arccos(\text{normal}(p) \cdot \text{normal}(n))$$

Assuming short distances and small angles due to the regularisation, this is an approximation to the curvature, $$\kappa = \frac{d\theta}{ds},$$

where θ is the angle between two normals and s is the arc length. The average of the absolute values of local estimations κ of the boundary points in the region of interest is chosen as the quantitative curvature estimate.

The local neighbourhood is defined as the immediate neighbours in the surface grid giving 8 neighbouring points. Given the resolution of the surface sampling, this neighbourhood is approximately 1.5 mm by 1.5 mm. Similar results are obtained if the neighbourhood is expanded slightly.

We extract the cartilage curvature as a single number by taking the mean value across a region of interest. This region is defined in terms of the coordinates from the shape model to be on the top surface (away from the bone) including the load-bearing region with a fairly large margin.

In order to investigate whether the cartilage loss is mainly an overall thinning or more present as focal lesions, we also measure the thickness of the thinnest part of the cartilage sheet (disregarding the location of this thinnest part). We use the term Cartilage Thickness Q10 for the 10% quantile of the measurements from the cartilage thickness map.

Analogous to the thickness map, we compute a surface curvature map for the cartilage sheet. The curvature is locally approximated by the change in cartilage surface normals in a small neighbourhood. The surface normals are given by the shape model.

The curvature map is illustrated in FIG. 13. Since the curvature of the model is dominant at the edges of the cartilage sheet (the crest of the shape model), we define a region of interest that includes the load-bearing region of the cartilage sheet but excludes the crest.

Since both the neighbourhood for approximating the local curvature as well as the region of interest is defined in terms of the coordinate system of the shape model, their sizes vary slightly between scans. On average, the neighbourhood is 3 by 3 mm (standard deviation 0.4 mm), and the region of interest is 16 by 24 mm (longest in the anterior posterior direction) with standard deviation 2 by 3 mm.

From hereon, we use the term cartilage curvature for the mean of the local curvature approximation across the load-bearing region of the cartilage sheet defined above. In another embodiment, we let super sampled volumes, as described in (Folkesson, J., Dam, E. B., Olsen, O. F., Pettersen, P., Christiansen, C.), from an automatic cartilage segmentation flow with mean curvature speed for a relatively smooth deformation of the surface from low towards higher scales, and evaluate the ability to discriminate between a healthy and an OA group.

The mean curvature flow for a surface S is $S_t = k_M N$ where $k_M$ is the mean curvature (the mean of the two principal curvatures), t is time and its subscript denotes differentiating, and N is the normal of S. The standard method for implementing surface evolution is the level set method, where the dynamics of a surface are represented as a dynamic level set of a function on a 3+1 dimensional domain. This function $\phi$(x,y,z;t) is an implicit representation of the surface at time t so that S(t)={(x,y,z)|φ(x,y,z;t)=0}. In the level set formulation the mean curvature flow is described by $$\phi_t = \kappa_M |\nabla\phi| = \left[\nabla\left(\frac{\nabla\phi}{|\nabla\phi|}\right)\right]|\nabla\phi|,$$

where $\nabla\phi$ is the gradient, thus the mean curvature can be written:

$$\kappa_M = (\phi_x^2(\phi_{yy} + \phi_{zz}) + \phi_y^2(\phi_{xx} + \phi_{zz}) + \phi_z^2(\phi_{xx} + \phi_{yy}) - 2(\phi_x\phi_y\phi_{xy} + \phi_x\phi_z\phi_{xz} + \phi_y\phi_z\phi_{yz}))/(\phi_x^2 + \phi_y^2 + \phi_z^2)^{3/2}$$

In terms of derivatives of φ. The derivatives are calculated using finite differences.

For curvature flow of curves in $\Re^2$ the Gage-Hamilton and Grayson theorems assure that convex non-intersecting curves will shrink smoothly to a point. This property does not extend to surfaces in $\Re^3$ where topology changes can occur. However, (Evans and Spruck) and (Chen, Giga and Goto) have independently proved existence, stability and uniqueness of viscosity solutions of the mean curvature motion for hypersurfaces in level sets.

The time behaviour of the curvature for curves is described by a reaction diffusion equation which is non-trivial to solve. For our surfaces, we examine the mean curvature behaviour throughout the flow, starting from tibial medial cartilage volumes from automatic segmentations, by taking the average of the absolute value of the mean curvature at the tibial medial articular surface. Reinitialisations are made every 7 iterations and the time step is 0.15. We super sample the scans, making 125 voxels of every voxel with a new resolution of approximately 0.16 mm voxel side length, which implies that the mean curvature flow will initially reduce partial volume effects.

Using shortening flow the surface curvature can be analysed at low scales, but when moving to higher scales as the flow continues the volume loses its cartilage like appearance and may change topology. Therefore we have developed another scheme for high scale curvature analysis where a deformable m-rep shape model is fitted to the cartilage. The m-rep represents an object by a mesh of medial atoms, each associated with a position, radius and directions to the boundary. Besides curvature analysis, the shape model is also used for finding anatomical correspondences and local thickness measures in a related study. As shown in FIG. 16 large points indicate medial atoms and small indicate boundary points. FIG. 16(b) shows the segmented cartilage it was fitted to and part of a sagittal slice with the tibial medial cartilage delineated is shown in FIG. 16(c).

The tibial medial cartilage model is fitted to the same set of automatic segmentations and consists of a mesh of 4×8 medial atoms, from which boundary points are interpolated on the articular surface with an average distance of approximately 0.7 mm. The deformable shape model framework shown in FIG. 16 ensures a regular, smooth boundary which makes it well suited for high scale curvature analysis. We define the load bearing (central) part of the articular surface as a region of interest and estimate the curvature locally in a 5×5 neighbourhood by taking the angle between the normals and divide it by distance between them. Assuming short distances and small angles due to the regularisation, this is an approximation to the curvature $$k = \frac{d\theta}{ds},$$

where θ is the angle between two normals and s is the arc length. The average of the absolute values of local estimations k of the boundary points in the region of interest is chosen as the quantitative curvature estimate. The principal curvatures are the maximal and minimal curvature associated with corresponding directions. For the model there are only 8 discrete directions to choose from, and the mean of the curvature estimates in these directions can be seen as an approximation to the mean curvature in the region.

In the test results of mean curvature flow, there is a rapid decrease in the average mean curvature on the articular surface initially as can be seen in FIG. 17. During this time the inter-scan reproducibility (defined as percent pairwise measurement differences) is low, and an unpaired t-test cannot separate a healthy group (KLi=0) from an OA group (KLi≧1) assuming a statistical significance level at 5%. This could be a result of the cancellation of partial volume effects present in the initial volume. As the flow propagates these values stabilize with curvature values of approximately 500 $m^{-1}$ and reproducibility of 5% pairwise difference (linear correlations coefficient around 0.4). In the separation between healthy and OA groups there is a minimum in p-values between 30-40 iterations. After 35 iterations the p-value is +0.0011 with inter-scan reproducibility of 6.3% pairwise difference with a linear correlation coefficient of 0.45 and average mean curvature of 660 $m^{-1}$ (±77 $m^{-1}$ s.d).

FIG. 18 illustrates how a cartilage sheet deforms during mean curvature flow. FIGS. 18a to 18b show the appearance after 0, 35, 100 and 200 iterations respectively.

The curvature estimation on the boundary points of the m-rep gives an average of 45 $m^{-1}$ (±9.7 $m^{-1}$ s.d), which is a factor of 10 lower than the values of the mean shortening flow method. The m-rep based method can separate the healthy from the OA group p=$2.6*10^{-4}$ and can even separate healthy from borderline OA (p=0.0085). The linear correlation coefficient for the inter-scan reproducibility is 0.68, with a pairwise difference in measurements of 11%. When estimating the curvature on the entire articular surface instead of only the load bearing part, the mean curvature is approximately the same, 46 $m^{-1}$ (±8.1 $m^{-1}$ s.d), but the method is no longer able to separate the healthy from the borderline OA group (p=030086). The linear correlation is decreased from 0.68 to 0.59 in the inter-scan reproducibility.

For an average medial tibial cartilage sheet, this region is approximately 1.7 cm wide (in medio-lateral direction) and 2.5 cm long (in anterior-posterior direction).

It may be noted that the tibial cartilage is to a first approximation quite flat in comparison to the femoral cartilage. However, as demonstrated here, its surfaces are locally curved to an extent that varies across the surface in question.

Cartilage volume is a quantification that can monitor the overall cartilage loss. The cartilage volume is computed directly from the segmentation by counting the number of voxels classified as belonging to the medial tibial cartilage sheet. For comparison, we also compute the cartilage volume from the manual segmentations performed by a radiologist.

Like cartilage volume, the cartilage area also aims at quantifying the overall cartilage loss. However, a combination of the two measurements can give a rough indication of whether the cartilage loss is an overall thinning (loss of volume, little loss of area) or a lesion-based loss with gaps and holes in the cartilage sheet (loss of volume, large loss of area).

The cartilage area is computed from the surface representation given by the cartilage shape model illustrated in FIGS. 11(a) and (b) (as the summation of the areas of the generated surface elements).

Note that the entire surface area of the cartilage sheet is included—both the area of the cartilage/bone interface and the area of the superior surface of the sheet.

We evaluated the precision/reproducibility of our quantifications by comparing the measures on pairs of scans of the same knee acquired with a week in between. We measured this in terms of linear correlation coefficient, mean relative absolute difference and coefficient of variation between the pairs of values.

We evaluated whether the quantifications are suitable for monitoring OA disease progression by checking if they allow separation of healthy and OA knees. This is done by performing an unpaired t-test on the values—the resulting p value estimates of the probability for the two groups not being different. Low p values, say below 0.05, shows a statistically significant separation of the two groups.

Also, in the same manner we check whether the quantifications allow separation of the healthy from the borderline/mild OA cases defined as KL=1 and KL=2 and finally evaluated whether separation of the healthy from the borderline OA cases (defined as KL1) is possible.

First, the graphs in FIG. 19 illustrate the performance of the narrowest joint gap quantification. Note that the distribution of the severity of OA in the evaluation population is available from the graph. In FIG. 19 the reproducibility of the measurement of the narrowest joint gap is illustrated on the left by the measurements performed on the pairs of scans acquired with a week in between. The linear correlation coefficient is 0.99, mean relative difference is 4.1%, coefficient of variation (CV) is 3.9%, and the mean absolute difference is 0.18 mm. On the right, the mean is shown (with bars illustrating the standard error of the mean) for healthy and OA and then for each KL score (note that the bar to the left for healthy is equal to the bar for KL=0, and that the bar OA is the combination of the three bars for KL=1, KL=2, and KL=3). The p value from an unpaired t-test gives the probability of the means for healthy and OA not being different to be 0.0050. The p value for healthy and "mild" OA not being different is 0.59.

The performances of simple, non-morphometric cartilage quantification measures, Cartilage Volume and Cartilage Surface Area, are illustrated analogously in FIGS. 20, 21 and 22. Each figure is analogous to FIG. 19. In FIG. 20, that shows cartilage volume (manual segmentation) against KL index, Left: Reproducibility is evaluated to linear correlation 0.90, mean relative difference 10.3%, CV 8.8%, and mean absolute difference 168 $mm^3$. Right: Separation of OA from healthy P values for healthy vs OA is 0.0016 and for healthy vs mild OA is 0.04. In FIG. 21, that shows cartilage volume (automatic segmentation) against KL index, Left: Reproducibility is evaluated to linear correlation 0.82, mean relative difference 8.8%, CV 10.1%, and mean absolute difference 173 $mm^3$. Right: Separation of OA from healthy P values for healthy vs OA is 0.0013 and for healthy vs mild OA is 0.04.

In FIG. 22, Left: Reproducibility is evaluated to linear correlation is 0.87, mean relative difference 6.3%, and CV 6.3%. Right: Separation of healthy from OA. P values for healthy vs OA is 0.00048 and for healthy vs mild OA is 0.03.

Finally, the performances of the morphometric quantifications, Cartilage Thickness, Cartilage Thickness Q10 and Cartilage Curvature, are illustrated analogously in FIGS. 23, 24 and 25. Each figure is analogous to FIG. 19. In FIG. 23, Left: Reproducibility is evaluated to linear correlation 0.84, mean relative difference 4.4%, CV 6.0%, and mean absolute difference 0.09 mm. Right: Separation of OA from healthy. P values for healthy vs OA is 0.0054 and for healthy vs mild OA is 0.07.

In FIG. 24, Left: Reproducibility is evaluated to linear correlation 0.86, mean relative difference 4.4%, CV 4.9%, and mean absolute difference 0.07 mm. Right: Separation of OA from healthy. P values for healthy vs OA is 0.00004 and for healthy vs mild OA is 0.01.

In FIG. 25, Left: Reproducibility is evaluated to linear correlation is 0.66, mean relative difference 8.9%, and CV 8.6%. Right: Separation of healthy from OA. P values for healthy vs OA is 0.00006 and for healthy vs mild OA is 0.0039.

The distance measures (narrowest joint gap and cartilage thickness) are normalized by the width of the tibial plateau when comparing the measures to the KS score. Analogously, volume and area are normalized by the tibial plateau width cubed and squared, respectively. This is a simple way of factoring out age, sex, and other causes that influence the size of the anatomical structures unrelated to the presence of OA.

The main results are summarized below. For each quantification measure, the precision is given as relative absolute difference, coefficient of variation, and linear correlation. The evaluation is performed on 31 scan-rescan pairs.

| Quantification | RelAbsDif | CV | Correlation |
|---|---|---|---|
| Joint Gap (manual from X-ray) | 4.0% | 3.9% | 0.99 |
| Volume (MT.VC.man) (manual from MRI) | 10.3% | 8.8% | 0.90 |
| Volume (MR.VC) | 8.8% | 10.1% | 0.82 |
| Area (MT.ACtAB) | 6.3% | 6.3% | 0.87 |
| Thickness (MR.ThCtAB) | 4.4% | 4.7% | 0.84 |
| ThicknessQ10 (MT.ThCtAB.Q10) | 4.4% | 4.9% | 0.86 |
| Curvature (MT.CuCtAB) | 8.9% | 8.6% | 0.66 |

The following table shows the results for the ability to separate groups of healthy knees from OA test subjects. In the test population there are 51 healthy (KL=0), 61 OA (KL above 0), 42 Mild OA (KL 1 or 2), and 28 Borderline OA (KL 1) subjects. The table shows p values from an unpaired t-test for each quantification method and for each group comparison.

| Quantification | Healthy vs All OA | Healthy vs Mild OA | Healthy vs Borderline |
|---|---|---|---|
| Joint Gap (manual from X-ray) | 0.0050 | 0.59 | 0.92 |
| Volume (MT.VC.man) (manual from MRI) | 0.0016 | 0.04 | 0.16 |
| Volume (MR.VC) | 0.0013 | 0.04 | 0.10 |
| Area (MT.ACtAB) | 0.00048 | 0.03 | 0.25 |
| Thickness (MR.ThCtAB) | 0.0054 | 0.07 | 0.11 |
| ThicknessQ10 (MT.ThCtAB.Q10) | 0.00004 | 0.01 | 0.18 |
| Curvature (MT.CuCtAB) | 0.00006 | 0.0039 | 0.006 |

Since the joint gap inspected from the X-ray is directly influencing the KL scores, it is reasonable to expect a close correlation between the narrowest gap measurements and the KL score. However, the more advanced, morphometric quantifications are comparable—or even better in the case of the cartilage curvature measure—in the ability to separate the healthy (KL=0) from the knees with OA (KL above 0). This is the case even though the more complex, automated measures are not quite as reproducible as the simple narrowest gap measurement. This indicates that the morphometric measures of cartilage shape actually do capture the disease progression better than the joint gap measurement. Further, the morphometric quantifications (thickness and curvature) show superior performance to the simpler, non-morphometric cartilage quantifications (volume and area).

However, the real potential of morphometric cartilage quantification is in the ability to detect the early stages of OA. Only the Cartilage Curvature quantification measure can distinguish the group of healthy knees from the group of knees with mild OA. Ideally, future treatments will focus on the early stages and prevent the occurrence of severe OA. Therefore, the ability to detect and quantify the early stages is essential for disease progression quantifications to be used in clinical studies.

Our proposed measure for cartilage curvature is an attempt at quantifying shape characteristics that are related to early disease progression and is a first step towards further research into the relations between joint biomechanics, bone structure, and cartilage. We focus the curvature measure on the central load-bearing part of the cartilage sheet and thereby get an indirect quantification of the effect of the shape of the underlying tibial bone.

At first sight it is very surprising that our cartilage curvature parameter reflecting cartilage curvature should be such a good tool for discriminating between healthy patients and those with early OA. However, on consideration, it is explicable.

The articular cartilage is in close relationship with the subchondral bone. The load distribution in the tibial surface seems to influence both cartilage thickness and remodelling as well as subchondral bone integrity. When the joint is spared from weight bearing, the cartilage begins to show a progressive thinning that will predispose to OA. (Cartilage atrophy in the knees of patients after seven weeks of partial load bearing. Hinterwimmer S, Krammer M, Krotz M, Glaser C, Baumgart R, Reiser M, Eckstein F. Arthritis Rheum. 2004 August; 50(8):2516-20.)

From that it would seem that the opposite could be true, meaning that the area where the main load is carried is where the cartilage shows itself thicker. Moreover, it has been demonstrated that despite the increased risk for OA in high BMI, this effect can be diminished by the misalignment of the knee that leads to a redistribution of the focal loading area (The effect of body weight on progression of knee osteoarthritis is dependent on alignment. Felson D T, Goggins J, Niu J, Zhang Y, Hunter DJ Arthritis Rheum. 2004 December; 50(12):3904-9.). Considering this, it is feasible that the areas receiving the higher pressure can vary depending upon the knee alignment and hence the cartilage thickness.

Another important factor to be taken into account is the remodelling of bone and cartilage. It seems to have a very close correlation between joint space narrowing and subchondral bone remodelling in osteoarthritis of the knees. Before the joint space diminishes the trabecular bone and subchondral cortical plates increase in thickness progressing afterwards with the diminishing of the joint space, leading in some cases to a corrugated cartilage surface that will end in a flat remodelled surface. This thicker trabecular bone is weaker than normal and the absorption of the local stresses have been suggested to lead to a subarticular osteoporosis. (Subchondral bone changes in hand and knee osteoarthritis detected by radiography. Christopher Buckland-Wright D. Sc Available online 5 Nov. 2003).

These findings strongly suggest that the bending of cartilage follows the course of the disease together with and perhaps depending upon the bone remodelling and that curvature can predict in some way how the bone will behave since there seems to exist a prior total degradation of cartilage in the areas where the bone will end up flat. Another point and not less important is the fact that the distribution of pressure in the joint space seems to behave differently when an osteochondral lesion is present. It was demonstrated that in lesions greater than 10 mm the area of pressure tends to localize nearby the lesion (Osteochondral defects in the human knee: influence of defect size on cartilage rim stress and load redistribution to surrounding cartilage. Guettler J H, Demetropoulos C K, Yang K H, Jurist Kans. Am J Sports Med. 2004 September; 32(6):1451-8. Epub 2004 Jul. 20). This could make cartilage more fragile in this area since the subjacent bone is weaker and be responsible for the beginning of a new curvature of the cartilage simply due to this redistribution of pressure.

In the process of this invention, the inventors have chosen to accept the KL score as the ground truth for OA progression. This is even if it is a somewhat simplified quantification. The KL score has been selected due to its relative simplicity and since it is generally accepted.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'.

REFERENCES

Abadie, E. Ethgen, D., Avouac, B., Bouvenot, G., Branco, J., Bruyere, O., Calvo, G., Devogelaer, J., Dreiser, R., Herrero-Beaumont, G., Kahan, A., Kreutz, G., Laslop. A., Lemmel. E., Nuki, G., Putte, L. V. D., Vanhaels, L. & Reginster, J. (2004). 'Recommendations for the use of new methods to assess the efficacy of disease-modifying drugs in the treatment of osteoarthritis', *Osteoarthritis and Cartilage* 12(4).

Amin, S., LaValley, M., Guermazi. A., Grigoryan. M., Hunter, D., Clancy, M., Niu, J., Gale, D. & Felson, D. (2005), 'The relationship between cartilage loss on magnetic resonance imaging and radiographic progression in men and women with knee osteoarthritis', *Arthritis and Rheumatism* 52(10).

Arya, S., Mount, D., Netanyahu, N., Silverman, R., Wu, A.: An optimal algorithm for approximate nearest neighbor searching in fixed dimensions. In: ACM-SIAM. Discrete Algorithms. Number 5 (1994)

Blum, H. & Nagel, R. (1978), 'Shape description using weighted symmetric axis features', *Pattern Recognition* 10(3), 167-180.

Christopher Buckland-Wright D. Sc Available online 5 Nov. 2003 Subchondral bone changes in hand and knee osteoarthritis detected by radiography.

Cootes, T., Taylor, C., Cooper, D. & Graham, J. (1995), 'Active shape models: Their training and application', *CVIU* (1), 38-59.

Cremers, D., Kohlberger, T. & Schnörr, C. (2002), Nonlinear shape statistics in mumford-shah based segmentation, in '7th European Conference on Computer Vision', Vol. 2351 of *Springer LNCS.*

Dam, E. B., Fletcher, P. T., Pizer, D. S. M., Tracton, G. & Rosenman, D. J. (2004), Prostate shape modeling based on principal geodesic analysis bootstrapping, in 'Proceedings of MICCAI 2004', Vol. 3216-3217 of *LNCS*, Springer.

Ding, C., Garnero, P., Cicuttini, F., Scott, F., Cooley, H. & Jones, G. (2005), 'Knee cartilage defects: association with early radiographic osteoarthritis, decreased cartilage volume, increased joint surface area and type ii collagen breakdown', *Osteoarthritis and Cartilage* 13.

Dunn, T., Lu, Y., Jin, H., Ries, M. & Majumdar, S. (2004), 'T2 relaxation time of cartilage at mr imaging: comparison with severity of knee osteoarthritis', *Radiology* 232(2).

Davies, R., Twining, C. Cootes, T., Waterton, J. & Taylor, C. (2002), 'A minimum description length approach to statistical shape modeling', *IEEE Transactions on Medical Imaging* 21(5).

Dice, L. (1945), 'Measures of the amount of ecologic association between species'. *Ecology* 26.

Felson D T, Goggins J, Niu J, Zhang Y, Hunter D J Arthritis Rheum. 2004 December; 50(12):3904-9. The effect of body weight on progression of knee osteoarthritis is dependent on alignment.

Fletcher, P. T., Joshi, S., Lu, C. & Pizer, S. M. (2003), Gaussian distributions on Lie groups and their application to statistical shape analysis. To appear *Information Processing in Medical Imaging.*

Fletcher, P. T., Lu, C. & Joshi, S. (2003), Statistics of shape via principal geodesic analysis on Lie groups, in 'Proc. of Computer Vision and Pattern Recognition'.

Folkesson, J., Dam, E. B., Olsen, 0. F., Pettersen, P. & Christiansen, C. (2005a), Automatic segmentation of the articular cartilage in knee mri using a hierarchical multiclass classification scheme, in 'Proceedings of MICCAI 2005'.

Folkesson, J., Dam, E., Olsen, O., Pettersen, P. & Christiansen, C. (2005b), Automatic quantification of articular cartilage from knee mr scans using surface smoothness as osteoarthritis indicator, in 'OARSI Conference Proceedings'.

Folkesson, J., Olsen, 0. F., Dam, E. B., Pettersen, P. C. & Christiansen, C. (2005), Combining binary classifiers for automatic cartilage segmentation in knee mri, in 'ICCV, Computer Vision for Biomedical Image Applications: Current Techniques and Future Trends'

Folkesson, J., Dam, E. B., Pettersen, P. C., Nielsen, M., Olsen, O. F., Christiansen, C.: Locating articular cartilage in mr images. In: Medical Imaging 2005: Image Processing. Proceedings of the SPIE. (2005)

Graichen, H., Eisenhart-Rothe, R. V., Vogl, T., Englmeier, K. H., Eckstein, F.: Quantitative assessment of cartilage status in osteoarthritis by quantitative magnetic resonance imaging. Arthritis and Rheumatism 50 (2004).

Grau, V., Mewes, A. U. J., Alcaniz, M., Kikinis, R. & Warfield, S. K. (2004), 'Improved watershed transform for medical image segmentation using prior information', *IEEE Trans. of Medical Imaging* 23(4).

Hinterwimmer S, Krammer M, Krotz M, Glaser C, Baumgart R, Reiser M, Eckstein F. Arthritis Rheum. 2004 August; 50(8):2516-20. Cartilage atrophy in the knees of patients after seven weeks of partial load bearing.

Hohe, J., Ateshian, G., Reiser, M., Englmeier, K. H., Eckstein, F. (2002) "Surface size, curvature analysis, and assessment of knee joint incongruity with mri invivo", *Magnetic Resonance in Medicine.*

Jones, G., Ding, C., Scott, F., Glisson, M. & Cicuttini, F. (2004), 'Early radiographic osteoarthritis is associated with substantial changes in cartilage volume and tibial bone surface area in both males and females', *Osteoarthritis and Cartilage* 12(2).

Joshi. S., Pizer, S. Fletcher, P. T., Yushkevich, P., Thall. A. & Marron, J. S. (2002), 'Multiscale deformable model segmentation and statistical shape analysis using medial descriptions', *Transactions on Medical Imaging* 21(5).

Kass, M., Witkin, A. & Terzopoulos, D. (1988), 'Snakes: Active contour models', *Int. Journal of Computer Vision* pp. 321-331.

Kamibayashi, L., Wyss, U., Cooke, T. & Zee, B. (1995), 'Changes in mean trabecular orientation in the medial condyle of the proximal tibia in osteoarthritis', *Calcif Tissue Int.* 57(1).

Kellgren, J. & Lawrence, J. (1957), 'Radiological assessment of osteo-arthrosis', *Ann Rheum Dis* 16(4).

Koo, S., Gold, G. & Andriacchi, T. (2005), 'Considerations in measuring cartilage thickness using mri: factors influencing reproducibility and accuracy', *Osteoarthritis and Cartilage* 13.

Loeuille, D., Olivier, P., Mainard, D., Gillet, P., Netter, P., Blum, A.: Magnetic resonance imaging of normal and osteoarthritic cartilage. Arthritis and Rheumatism 41 (1998)

Lynch, J. A., Zaim, S., Zhao, J., Stork, A., Peterfy, C. G. & Genant, H. K. (2001), Automatic measurement of subtle changes in articular cartilage from mri of the knee by combining 3d image registration and segmentation, in 'SPIE, Medical Imaging', Vol. 4322.

McWalter, E. Wirthz, W., Siebert, M., von Eisenhart-Rothe, R., Hudelmaier, M., Wilson, D. & Eckstein, F. (2005), 'Use of novel interactive input devices for segmentation of articular cartilage from magnetic resonance images', *Osteoarthritis and Cartilage* 13.

Messent, E., Ward, R., Tonkin, C. & Buckland-Wright, C. (2005), 'Tibial cancellous bone changes in patients with knee osteoarthritis a short-term longitudinal study using fractal signature analysis1', Osteoarthritis and Cartilage 13.

Muensterer, O., Eckstein, F., Hahn, D., Putz, R.: Computer-aided three dimensional assessment of kneejoint cartilage with magnetic resonance imaging. Clinical Biomechanics 11 (1996)

Pakin, S. K., Tamez-Pena, J. G., Totterman, S. & J. Parker, K. (2002), Segmentation, surface extraction and thickness computation of articular cartilage, in 'SPIE, Medical Imaging', Vol. 4684, pp. 155-166.

Pizer, Chen, Fletcher, Fridman, Fritsch, Gash, Glotzer, Jiroutek, Joshi, Muller, Thall, Tracton, Yushkevich & Chaney (2003), 'Deformable m-reps for 3d medical image segmentation', *IJCV*

Pizer, S., Fritsch, D., Yushkevich, P., Johnson, V. & Chaney, E. (1996), 'Segmentation, registration, and measurement of shape variation via image object shape', *IEEE Transactions on Medical Imaging* 18(10).

Stammberger, T., Eckstein, F., Michaelis, M., Eng/meier, K.-H. & Reiser, M. (1999), 'Interobserver reproducibility of quantitative cartilage measurements: Comparison of b-spline snakes and manual segmentation', *Magnetic Resonance Imaging* 17(7).

Tamez-Pena, J. G., Barbu-Mcinnis, M. & Totterman. S. (2004), Knee cartilage extraction and bone-cartilage interface analysis from 3d mri data sets. in 'SPIE, Medical Imaging', Vol. 5370.

Terukina, M., Fujioka, H., Yoshiya, S., Kurosaka, M., Makino, T. Matsui, N., Tanaka, J. (2003) "Analysis of the thickness and curvature of articular cartilage of the femoral condyle" *Athroscopy* 10 969-973.

Thall, A. (2002), Fast $C^2$ interpolating subdivision surfaces using iterative inversion of stationary subdivision rules, Technical report, University of North Carolina. http:flmi-dag.cs.unc.edu/pubs/papers/Thall_TR02-001.pdf.

Thodberg, H. H. (2003), Minimum description length shape and appearance models, in 'Information Processing in Medical Imaging', number 2732 in 'LNCS', Springer.

Thodberg, H. H. & Olafsdottir, H. (2003), Adding curvature to minimum description length shape models, in 'Proc of British Machine Vision Conference'.

Tracton, G., Chaney, E., Rosenman, J. & Pizer, S. (1994), Mask: combining 2d and 3d segmentation methods to enhance functionality, in 'Proceedings of Mathematical Methods in Medical Imaging III', Vol. SPIE Vol 2299.

The invention claimed is:

1. A method for the analysis of three dimensional scan data representing an articular cartilage to extract a quantitative parameter indicative of joint pathology, which method comprises determining a measure of the local curvature of the cartilage within a region of interest, and further comprising comparing the measured value of said quantitative parameter for the joint with values of the quantitative parameter previously established in respect of joints characterized by a pathology.

2. The method as claimed in claim 1, wherein the method comprises determining a measure of the 3D local curvature at a scale arranged to result in a measure of curvature above 40 $m^{-1}$.

3. The method as claimed in claim 2, wherein said scale is arranged to result in a measure of curvature between 40 $m^{-1}$ and 200 $m^{-1}$.

4. The A method as claimed in claim 1, wherein said region of interest lies in a load bearing area of said cartilage.

5. The method as claimed in claim 1, wherein the region of interest is selected to lie in an interior region of a cartilage sheet separated from the edges of said sheet.

6. The method as claimed in claim 1, wherein said cartilage is a knee cartilage.

7. The method as claimed in claim 4, wherein said knee cartilage is a tibial cartilage.

8. The method as claimed in claim 5, wherein said tibial cartilage is a medial tibial cartilage.

9. The method as claimed in claim 1, wherein a comparison of said quantitative parameter is made both with values of the quantitative parameter previously established in respect of healthy joints and with values of said quantitative parameter previously established in respect of joints characterized by a pathology.

10. The method as claimed in claim 6, wherein said pathology is osteoarthritis, rheumatoid arthritis, villonodular synovitis, Lipoid dematoarthritis (Multicentric reticulohistiocytosis), Enteropathic arthritis, hemophilia (intraarticular bleeding), Gout, Familial Mediterranean fever, Pseudogout, Ochronotic arthropathy, Secondary osteoarthritis, Syphilis (tabes dorsalis), Pyrogenic arthritis, Tuberculous arthritis or Fungal arthritis.

11. The method as claimed in claim 1, wherein said three dimensional scan data is produced by magnetic resonance imaging (MRI).

12. The method as claimed in claim 8, wherein said quantitative parameter is derived from changes between adjacent locations within the region of interest in directions defined with respect to normals to a selected cartilage surface or interior contour.

13. The method as claimed in claim 12, wherein the changes in the directions of normals are weighted by the inverse distance to the local centre point.

14. The method as claimed in claim 1, wherein said quantitative parameter represents an average of said changes in direction over said region of interest.

15. The method as claimed in claim 12, wherein said quantitative parameter is quantitatively related to the average value over the region of interest of 'curvature (p)' given for each point p in the region of interest by the expression:

$$\text{curvature}(p) = \frac{1}{|N|} \sum_{n \in N} a\cos(\text{normal}(p) \cdot \text{normal}(n))$$

reflecting the mean angle between the surface normal at surface point p with a neighborhood set N and the normals at the neighboring surface points n.

16. The method as claimed in claim 12, wherein points p are sampled at a spacing of from 0.2 to 2 mm in evaluating said average value of curvature(p).

17. The method as claimed in claim 15, wherein said neighborhood set N of neighboring points for any point P occupies an area of from 1 $mm^2$ to 4 $mm^2$.

18. The method as claimed in claim 9, wherein said quantitative parameter is derived from changes in mean curvature flow over the region of interest taken from the maximal and minimal curvature associated with corresponding directions.

19. The method as claimed in claim 15, wherein said mean curvature flow is calculated by iteratively calculating the average of the absolute value of mean curvature at an articular surface.

20. The method as claimed in claim 1, wherein said region of interest is from 1 $cm^2$ to 8 $cm^2$ in area.

21. The method as claimed in claim 1, further comprising combining said measure of local curvature with one or more of (a) a measure of cartilage volume, (b) a measure of cartilage thickness, and (c) a measure of cartilage smoothness, to provide an improved discrimination between said combined measure when representing joint pathology and equivalent measures derived from healthy joints.

22. The method as claimed in claim 1, further comprising analyzing said scan data to perform an automatic segmentation of image data representing cartilage from bone and other background prior to extracting said quantitative parameter.

23. The method as claimed in claim 1, wherein a value for said quantitative parameter which is higher than that established for healthy joints is taken as indicative of probable joint pathology.

24. The method as claimed in claim 1, further comprising normalizing the position of the knee prior to segmentation.

* * * * *